(12) United States Patent
Li et al.

(10) Patent No.: US 8,796,421 B2
(45) Date of Patent: Aug. 5, 2014

(54) HUMAN EPIDERMAL GROWTH FACTOR RECEPTOR VARIANT LACKING AN EXON

(75) Inventors: Zonghai Li, Shanghai (CN); Min Zhou, Shanghai (CN); Hai Wang, Shanghai (CN); Bizhi Shi, Shanghai (CN); Shengli Yang, Shanghai (CN); Hongyang Wang, Shanghai (CN); Jianren Gu, Shanghai (CN)

(73) Assignee: Shanghai Cancer Institute, Shanghai (CN)

( * ) Notice: Subject to any disclaimer, the term of this patent is extended or adjusted under 35 U.S.C. 154(b) by 0 days.

(21) Appl. No.: 13/879,538

(22) PCT Filed: Oct. 24, 2011

(86) PCT No.: PCT/CN2011/081162
§ 371 (c)(1),
(2), (4) Date: May 23, 2013

(87) PCT Pub. No.: WO2012/048667
PCT Pub. Date: Apr. 19, 2012

(65) Prior Publication Data
US 2013/0236465 A1    Sep. 12, 2013

(30) Foreign Application Priority Data
Oct. 15, 2010  (CN) .......................... 2010 1 0510056

(51) Int. Cl.
*C07K 1/00* (2006.01)
*C07K 14/00* (2006.01)
*C07K 17/00* (2006.01)

(52) U.S. Cl.
USPC ........................................................ 530/350

(58) Field of Classification Search
None
See application file for complete search history.

(56) References Cited

FOREIGN PATENT DOCUMENTS

CN           1676166 A        10/2005

OTHER PUBLICATIONS

Andl CD, et al. J. Biol. Chem. 278(3):1824-1830, Jan. 17, 2003.*
International Search Report from Application PCT/CN2011/081162, dated Feb. 16, 2012, 8 pages.
Identification of an Exon 4-Deletion Variant of Epidermal Growth Factor Receptor with Increased Metastasis-Promoting Capacity, Neoplasia, (2011) 13, pp. 461-471.
GenBank: HQ912715.1, Mar. 27, 2011, 4 pages.
GenBank: AY888086.1, Mar. 21, 2005, 3 pages.
GenBank: CAA25240.1, Oct. 7, 2008, 4 pages.
M.A. Adelsman et al., "Ligand-Independent Dimerization of Oncogenic v-erbB Products Involves Covalent Interactions," Journal of Virology, vol. 70, No. 4 (Apr. 1996), p. 2533-2544.
A.J.L. Clark et al., "Epidermal growth factor regulates the expression of its own receptor," Proc. Natl. Acad. Sci. USA, vol. 82 (Dec. 1985), p. 8374-8378.
T. Gilmore et al., "Protein Phosphorylation at Tyrosine Is Induced by the v-erbB Gene Product In Vivo and In Vitro," Cell, vol. 40 (Mar. 1985), p. 609-618.
J. Ishikawa et al., "Amplification and Overexpression of the Epidermal Growth Factor Receptor Gene in Human Renal-Cell Carcinoma," Int. J. Cancer, vol. 45 (1990), p. 1018-1021.
K. Khazaie et al., "Truncation of the human EGF receptor leads to differential transforming potentials in primary avian fibroblasts and erythroblasts," The EMBO Journal, vol. 7, No. 10 (1988), p. 3061-3071.
C-T Kuan et al., "EGF mutant receptor vIII as a molecular target in cancer therapy," Endocrine-Related Cancer, vol. 8 (2001), p. 83-96.
T. A. Libermann et al., "Amplification, enhanced expression and possible rearrangement of EGF receptor gene in primary human brain tumours of glial origin," Nature, vol. 313 (Jan. 10, 1985), p. 144-147.
T.A. Libermann et al., "Amplification and Overexpression of the EGF Receptor Gene in Primary Human Gioblastomas," J. Cell Sci. Suppl., vol. 3 (1985), p. 161-172.
S-H Lu et al., "Amplification of the EGF Receptor and c-*myc* Genes in Human Esophageal Cancers," Int. J. Cancer, vol. 42 (1988), p. 502-505.
M.W. Pedersen et al., "The type III epidermal growth factor receptor mutation," Annals of Oncology, vol. 12 (2001), p. 745-760.
J. Ro et al., "Amplified and Overexpressed Epidermal Growth Factor Receptor Gene in Uncultured Primary Human Breast Carcinoma," Cancer Research, vol. 48 (Jan. 1, 1988), p. 161-164.
K. Schwechheimer et al., "EGFR Gene Amplification—Rearrangement in Human Glioblastomas," Int. J. Cancer, vol. 62 (1995), p. 145-148.
M. Viana-Pereira et al., "Analysis of EGFR Overexpression, *EGFR* Gene Amplification and the EGFRvIII Mutation in Portuguese Highgrade Gliomas," Anticancer Research, vol. 28 (2008), p. 913-920.
H. Wang et al., "Epidermal growth factor receptor vIII enhances tumorigenicity and resistance to 5-fluorouracil in human hepatocellular carcinoma," Cancer Letters, vol. 279 (2009), p. 30-38.
K. Yoshida et al., "Amplification of epidermal growth factor receptor (EGFR) gene and oncogenes in human gastric carcinomas," Virchows Archiv B Cell Pathol, vol. 57 (1989), p. 285-290.
M. Zhou et al., "EGFRvIII mRNA detection in the serum of patients with hepatocellular carcinoma," Liver International (2010), p. 925-927.

* cited by examiner

*Primary Examiner* — Robert Landsman
(74) *Attorney, Agent, or Firm* — Hamre, Schumann, Mueller & Larson, P.C.

(57) ABSTRACT

The present invention provides an epidermal growth factor receptor variant-de4 EGFR protein. The variant lacks the fourth exon of the epidermal growth factor receptor, and promotes tumor cell invasion/metastasis. The present invention also provides an encoding gene for the variant and a method of producing the variant by means of recombination technology.

8 Claims, 8 Drawing Sheets

HUMAN EPIDERMAL GROWTH FACTOR RECEPTOR VARIANT LACKING AN EXON

FIELD OF INVENTION

The present invention relates to the field of biological technology and medicine. Particularly, the present invention relates to a new polynucleotide encoding human EGFR variant de4 EGFR (Epidermal growth factor receptor with Exon 4 deletion, de4 EGFR) and the polypeptide encoded from this polynucleotide. The invention further relates to the application and preparation of this polynucleotide and polypeptide.

BACKGROUND OF INVENTION

Epidermal growth factor receptor (EGFR) is a 170 kilodalton membrane glycoprotein product of proto-oncogene c-erb B. EGFR gene is acellular homolog of the erb B oncogene originally identified in avian erythroblastosis viruses[1]. Activation of this oncogene by gene amplification has been observed in a variety of human tumors[2-8].

EGFR has been demonstrated to be overexpressed in many types of human solid tumors[9], including lung, colon, breast, gastric, brain, bladder, head and neck, ovarian, kidney and prostate carcinomas[9]. One major difference between v-erb B oncogenes and the normal EGFR gene is that the viral oncogenes are amino-truncated versions of the normal receptor: they lack most of the extracytoplasmic domain but remain the transmembrane and tyrosine kinase domains[10], which results that it is unable to bind epidermal growth factor (EGF) but still can phosphorylate other proteins[11, 12].

A variety of genetic alterations can occur in viral erb B oncogenes, e.g. substitutions and deletions of amino acids at the carboxyl terminus of the gene, wherein amino terminus truncation is critical to carcinogenesis. Amino terminus truncation is a feature of most of v-erb B oncogenes, including that arised by promoter insertion or retroviral transduction. In contrast, carboxy terminus deletions appear to be associated only with tumors arised through retroviral transduction and seem to be determined by host range and tumor type specificity. Transfection experiments conducted with amino-terminus-truncated avian c-erb B genes or human EGF receptors demonstrate that such truncation is able to create cell transformation[13].

Amplification of EGFR gene occurs in 40-50% of the malignant human gliomas[14-16]. Rearrangement of the receptor gene is evident in many tumors with gene amplification. The rearrangement seems to affect the amino terminus of the gene more[17-20].

At present, eight major variants of EGFR are known: 1) EGFRvI lacks a majority of the extracellular domain of EGFR. 2) EGFRvII consists of an 83aa in-frame deletion in the extracellular domain of EGFR. 3) EGFRvIII consists of a 267aa in-frame deletion in the extracellular domain of EGFR. 4) EGFRvIV contains deletions in the cytoplasmic domain of EGFR. 5) EGFRvV contains deletions in the cytoplasmic domain of EGFR. 6) EGFR.TDM/2-7 contains a duplication of exons 2-7 in the extracellular domain of EGFR. 7) EGFR.TDM/18-26 contains a duplication of exons 18-26 in the extracellular domain of EGFR. 8) In addition, there is a second EGFRvIII mutant (EGFRvIII/Δ12-13) that possesses a novel deletion of histidine residue at the junction of exons 11 and 14[21] (FIG. 1).

EGFRvIII is the most commonly occurring variant of the epidermal growth factor (EGF) receptor in human cancers [22]. During the process of gene amplification, deletion of 267 amino acids occurs in the extracellular domain, which creates a novel junction (glycine). EGFRvIII is not known to be expressed in any normal tissues[22]. Yet, EGFRvIII expresses in many tumor cells, e.g., 78% breast cancer, 50~70% gliomas, 16% NSCL cancers and 73% ovarian cancers[22]. Furthermore, EGFRvIII expression was also found in hepatocellular carcinoma by the inventor's lab recently[23, 24].

However, up to now, understanding of the reasons and mechanisms for cancer invasion and metastasis is not sufficient enough. Therefore, it is urgently necessary to develop the proteins associated with tumor invasion and metastasis in the art,

SUMMERY OF INVENTION

The purpose of the invention is to provide a novel epidermal growth factor receptor variant de4 EGFR polypeptide related to tumor invasion and metastasis, and fragments, analogs and derivates thereof.

Another purpose of the invention is to provide a polynucleotide encoding these polypeptides.

Another purpose of the invention is to provide a method for producing these polypeptides and an application of the polypeptides and its encoding sequence.

The first aspect of the present invention is to provide a novel isolated de4 EGFR polypeptide, which includes polypeptide comprising amino acid sequence of SEQ ID NO: 2, or the conserved variant polypeptide thereof, or the active fragment thereof, or the active derivate thereof.

Preferably, the polypeptide is selected from the following groups:

(a) Polypeptide comprising the amino acid sequence of SEQ ID NO: 2;

(b) Polypeptide generated by replacement, deletion or addition of the amino acid sequence in SEQ ID NO: 2 with one or more amino acids (preferably 1-10 amino acids), which can promote tumor cell invasion and/or migration and is derived from (a).

(c) Polypeptide possessing ≥95% homology to the amino acid sequence of SEQ ID NO: 2, which can promote tumor cell invasion or migration and is derived from (a).

More preferably, the amino acid sequence of the polypeptide is shown as SEQ ID NO: 2.

The de4 EGFR mutant is deleted of exon 4 of epidermal growth factor receptor and a new amino acid (glycine) is generated at the junction.

The second aspect of the present invention is to provide a polynucleotide encoding these isolated polypeptides, which contains a nucleotide sequence possessing at least 80% homology (preferably at least 90% homology, more preferably at least 95% homology, more preferably at least 98% homology) to one nucleotide sequence selected from the following groups: (a) a polynucleotide encoding human de4 EGFR polypeptide above-mentioned and (b) a polynucleotide complementary to the polynucleotide (a). Preferably, the polynucleotide encodes the polypeptide with the amino acid sequence shown as SEQ ID NO: 2. More preferably, the sequence of the polynucleotide is selected from one of the following groups: (a) sequence of $1^{st}$-$3495^{th}$ nucleotide in SEQ ID NO: 1; (b) $1^{st}$-$3498^{th}$ sequence of $1^{st}$-$3498^{th}$ nucleotide in SEQ ID NO: 1.

The third aspect of the present invention is to provide a vector containing the polynucleotide above-mentioned, and host cells transformed or transduced by the vector or host cells directly transformed or transduced by the above-mentioned polynucleotide. Preferably, the genetically engineered host cell contains said vector or its chromosome is integrated with the polynucleotide according to the second aspect.

The fourth aspect of the present invention is to provide a method for preparing the polypeptide with the activity of human de4 EGFR protein. The method comprises: (a) under the appropriate condition for expressing human de4 EGFR protein, culture the transformed or transduced host cell; (b) the polypeptide with the activity of human de4 EGFR protein is separated from the culture.

The fifth aspect of the present invention is to provide an antibody specifically binding to human de4 EGFR polypeptide.

The sixth aspect of the present invention is to provide compounds mimicking, stimulating and antagonizing the activity of human de4 EGFR polypeptide and compounds inhibiting the expression of human de4 EGFR polypeptide. The invention also provides a method for screening and/or preparing these compounds. Preferably, the compounds are the antisense sequences of the sequence encoding human de4 EGFR polypeptide or fragments thereof.

The seventh aspect of the present invention is to provide a method for detecting whether de4 EGFR protein is present in samples (especially non-diagnostic detection in vitro), which includes: contact the antibody specific to de4 EGFR and the sample, observe the formation of antibody complex, and if an antibody complex forms, it indicates that de4 EGFR protein is present in the sample.

The eighth aspect of the present invention is to provide a method for detecting the diseases or the sensitivity thereof related to abnormal expression of human de4 EGFR polypeptide (like tumor sensitivity). The method includes: detect whether there are mutations in the nucleotide sequence encoding said polypeptide.

The ninth aspect of the present invention is to provide an application of the polypeptide and the encoding sequence of the invention. For example, the polypeptide of the invention can be used to screen the agonists for activating human de4 EGFR polypeptide or the antagonists for suppressing human de4 EGFR polypeptide or to identify a peptide fingerprint. The sequence encoding human de4 EGFR protein of the invention or fragments thereof can be used as the primers for PCR amplification, or as the probes for hybridization reaction, or to produce gene arrays or microarrays.

The tenth aspect of the present invention is to provide a pharmaceutical composition, containing a safe and effective dosage of the antagonist for human de4 EGFR polypeptide of the invention and pharmaceutically acceptable carriers. These pharmaceutical compositions can be used to treat diseases such as breast cancer, gliomas and so on.

In another preferred embodiment, said antagonist is the antibody specifically binding to de4 EGFR polypeptide and not binding to human epidermal growth factor receptor.

The eleventh aspect of the present invention is to provide a method for determining whether a tested compound is an antagonist or agonist for de4 EGFR polypeptide, wherein it includes steps:

(a) The tested compound is added to the tumor cell culture system in vitro as a test group, the same tumor cell cultured in vitro is set as a control group, wherein said tumor cell is from mammals and expresses this invented de4 EGFR polypeptide.

(b) Observe the degree of tumor cell migration/invasion in test group and control group. If the degree of tumor cell migration/invasion is higher in test group than that in control group, it indicates the tested compound is an agonist for de4 EGFR polypeptide. If the degree of tumor cell migration/invasion is lower in test group than that in control group, it indicates the tested compound is an antagonist for de4 EGFR polypeptide.

In another preferred embodiment, said tumor cell is from human.

Regarding the techniques disclosed in the invention, the other aspects of the invention is obvious to the skilled in the art.

DESCRIPTION OF FIGURES

The following figures are used to illustrate the detail embodiments of the invention, but not to limit the scope of the invention.

DETAILED DESCRIPTION OF INVENTION

Figure 1:
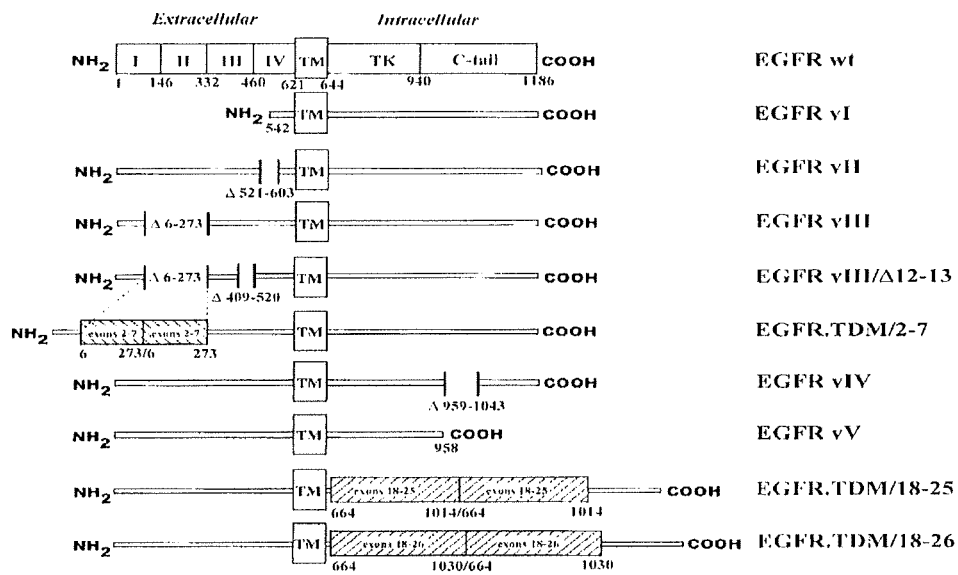
FIG. 1 shows wild-type EGFR and various mutants thereof. In the figure, exon(s) represent(s) exon(s); C-tail represents C terminus.

After wide and thorough studies, the inventor first discovered and isolated a novel EGFR variant with deletion of exon (de4 EGFR), possessing the following features: 1) It lacks the exon 4 sequence in extracellular domain of epidermal growth factor receptor and have a novel amino acid (glycine) generated at the junction. 2) It presents in various cancer tissues but not in normal tissues. 3) It promotes the tumor cell invasion and metastasis significantly in vitro. 4) It promotes the tumor cell invasion and metastasis significantly in vivo. Based on this discovery, the inventors completed the present invention.

In the invention, the terms "de4 EGFR protein", "de4 EGFR polypeptide" and "epidermal growth factor receptor (deletion) variant de4 EGFR" can be used interchangeably. They all mean the proteins or polypeptides having the amino acid sequence of human epidermal growth factor receptor (EGFR) variant de4 EGFR (SEQ ID NO:2). They contain EGFR variant de4 EGFR carrying initial methionine or not.

As used herein, "isolated" means to isolate substance from its primitive environment (if it is a natural substance, then its primitive environment is natural environment). Polynucleotide and polypeptide is not isolated and purified in the living cells which are under the natural state, but the same polynucleotide or polypeptide is isolated if it is separated from other substance both present in the same environment from the natural state.

As used herein, the terms "isolated De4 EGFR protein or polypeptide" mean that De4 EGFR polypeptide does not essentially contain other proteins, lipids, carbohydrate or any other substances associated therewith in nature. The skilled in the art can purify De4 EGFR protein by standard protein purification techniques. Essentially purified polypeptide forms a single main band on a non-reductive PAGE gel. The purity of De4 EGFR polypeptide can be analyzed by amino acid sequence analysis.

The polypeptide of invention may be a recombinant polypeptide, natural polypeptide, or synthetic polypeptide, preferably a recombinant polypeptide. The polypeptide of invention may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the protocol of recombinant production, the polypeptide of invention may be glycosylated or non-glycosylated. The polypeptide of invention may or may not comprise the starting Met residue.

The invention further comprises the fragments, derivatives and analogues of De4 EGFR. As used in the invention, the terms "fragment", "derivative" and "analogue" mean the polypeptide that essentially retains the same biological functions or activity of De4 EGFR protein of the invention. The fragment, derivative or analogue of the polypeptide of invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretary sequence or a sequence which is employed for purification of the mature polypeptide or a proprotein sequence, e.g., a fusion protein formed with IgC fragment. Such fragments, derivatives and analogs are deemed to be within the scope of those skilled in the art from the teachings herein.

In the present invention, the term "human De4 EGFR polypeptide" refers to a polypeptide having the activity of human De4 EGFR protein comprising the amino acid sequence of SEQ ID NO: 2. The term also comprises the variants of said amino acid sequence which have the same function of human De4 EGFR. These variants include, but are not limited to, deletions, insertions and/or substitutions of several amino acids (typically 1-50, preferably 1-30, more preferably 1-20, most preferably 1-10), and addition of one or more amino acids (typically less than 20, preferably less than 10, more preferably less than 5) at C-terminal and/or N-terminal. For example, the protein functions are usually unchanged when an amino residue is substituted by a similar or analogous one. Further, the addition of one or several amino acids at C-terminal and/or N-terminal will not change the function of protein. The term also includes the active fragments and derivatives of De4 EGFR protein.

The variants of polypeptide include homologous sequences, allelic variants, natural mutants, induced mutants, proteins encoded by DNA which hybridizes to De4 EGFR DNA under high or low stringency conditions as well as the polypeptides or proteins retrieved by antisera raised against De4 EGFR polypeptide. The present invention also provides other polypeptides, e.g., fusion proteins, which include the De4 EGFR polypeptide or fragments thereof. In addition to substantially full-length polypeptide, the soluble fragments of De4 EGFR polypeptide are also included. Generally, these fragments comprise at least 10, typically at least 30, preferably at least 50, more preferably at least 80, most preferably at least 100 consecutive amino acids of De4 EGFR polypeptide. It should be understood that the variant forms of polypeptides of the invention don't include the wild-type EGFR and the mutants thereof known in the art as shown in FIG. 1.

The present invention also provides the analogues of De4 EGFR protein or polypeptide. Analogues can differ from naturally occurring De4 EGFR polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

In the invention, "De4 EGFR conservative mutant" means a polypeptide formed by substituting at most 10, preferably at most 8, more preferably 5, and most preferably at most 3 amino acids with the amino acids having substantially the same or similar property, as compared with the amino acid sequence of SEQ ID NO: 2. Preferably, these conservative mutants are formed by the substitution according to Table 1.

TABLE 1

| primary residue | usual replacement | preferred replacement |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |

The polynucleotide according to the invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NO: 1, or is a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 1.

The sequences encoding the mature polypeptide of SEQ ID NO: 2 include those encoding only the mature polypeptide, those encoding mature polypeptide plus various additional encoding sequence, the encoding sequence for mature polypeptide plus the non-encoding sequence and optional additional encoding sequence.

The term "polynucleotide encoding the polypeptide" includes the polynucleotide encoding said polypeptide and the polynucleotide comprising additional and/or non-encoding sequence.

The invention further relates to the variants of the hereinabove polynucleotides which encode a polypeptide having the same amino acid sequence of invention, or its fragment, analogue and derivative. The variant of the polynucleotide may be a naturally occurring allelic variant of the polynucleotide or a non-naturally occurring variant of the polynucleotide. Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The present invention further relates to polynucleotides, which hybridize to the hereinabove-described sequences, if there is at least 50%, preferably at least 70%, more preferably at least 80%, and most preferably at least 90% or at least 95% identity between the sequences. The present invention particularly relates to polynucleotides, which hybridize under stringent conditions to the polynucleotides of the invention. As herein used, the term "stringent conditions" means the following conditions: (1) hybridization and washing under low ionic strength and high temperature, such as 0.2×SSC, 0.1% SDS, 60° C.; (2) hybridization after adding denaturants, such as 50% (v/v) formamide, 0.1% bovine serum/0.1% Ficoll, 42° C.; or (3) hybridization of two sequences sharing at least 90%, preferably more than 95% homology. Further, the polynucleotides which hybridize to the hereinabove described polynucleotides encode a polypeptide which retains the same biological function or activity as the mature polypeptide as set forth in SEQ ID NO: 2.

The invention also relates to nucleic acid fragments hybridized with the hereinabove sequence. As used in the present invention, the length of the "nucleic acid fragment" is at least 15 bp, preferably at least 30 bp, more preferably at least 50 bp, and most preferably at least 100 bp. The nucleic acid fragment can be used in the amplification techniques of nucleic acid, e.g., PCR, so as to determine and/or isolate the polynucleotide encoding de4 EGFR protein.

The polypeptide and polynucleotide of the invention are preferably in isolated form, preferably purified to be homogenous.

The full-length sequence of human de4 EGFR nucleotide or the segment thereof usually can be obtained by PCR amplification, recombination or artificial synthesis. For PCR amplification, prime can be designed according to nucleotide sequence disclosed in the invention, specifically the sequence of open reading frame, and the template can be cDNA library purchased commercially or prepared by the conventional methods known in the art, then conduct the amplification thereby obtaining the concerned sequence. When the sequence is relatively long, usually twice or more times of PCR amplification is necessary and then merge the segment amplified respectively according to the correct sequence.

Once the concerned sequences are obtained, they can be obtained in abundance by recombination methods. Generally, they are cloned into vectors, introduced into cells and then separated from the proliferated host cells by conventional methods.

Moreover, the concerned sequences can be synthesized artificially, especially when the segment length is shorter. Usually, several small segments are synthesized primarily and then the long segments can be obtained by ligation.

Nowadays, the DNA sequence encoding the protein of the invention (or the segments, or the derivates thereof) can be completely obtained by chemical synthesis, which can be introduced to various DNA molecules (or vectors) and cells known in the art. Additionally, the mutations can be introduced to the protein sequence of the invention by chemical synthesis.

The method of amplification of DNA/RNA by PCR (Saiki, et al. Science 1985; 230:1350-1354) is preferably used to obtain the gene of the invention. Especially when it is difficult to obtain the full-length cDNA, the method of RACE is preferably used. The primers used in PCR can be properly selected according to the polynucleotide sequence information of invention disclosed herein and synthesized by the conventional methods. The amplified DNA/RNA fragments can be isolated and purified by conventional methods such as gel electrophoresis.

The invention further relates to a vector comprising the polynucleotide of the invention, a genetic engineered host cell transformed with the vector of the invention or directly with the sequence encoding De4 EGFR protein, and the method for producing the polypeptide of invention by recombinant techniques.

The recombinant human De4 EGFR polypeptides can be expressed or produced by the conventional recombinant DNA technology (Science, 1984; 224:1431), using the polynucleotide sequence of invention. Generally, it comprises the following steps:

(1) transfecting or transforming the appropriate host cells with the polynucleotide encoding De4 EGFR polypeptide of the invention or the vector containing said polynucleotide;

(2) culturing the host cells in an appropriate medium;

(3) isolating or purifying the protein from the medium or cells.

In the present invention, the polynucleotide sequences encoding human de4 EGFR protein may be inserted into a recombinant expression vector. The term "expression vector" refers to a bacterial plasmid, bacteriophage, yeast plasmid, plant virus or mammalian cell virus, such as adenovirus, retrovirus or any other vehicle known in the art. Vectors suitable for use in the present invention include, but are not limited to, the T7-based expression vector for expression in bacteria (Rosenberg, et al., Gene, 56:125, 1987), the pMSXND expression vector for expression in mammalian cells (Lee and Nathans, J Biol. Chem., 263:3521, 1988) and baculovirus-derived vectors for expression in insect cells. On the whole, any plasmid or vector can be used to construct the recombinant expression vector as long as it can replicate and is stable in the host. One important feature of expression vector is that the expression vector typically contains an origin of replication, a promoter, a marker gene as well as the translation regulatory components.

The methods known by the artisans in the art can be used to construct an expression vector containing the DNA sequence of de4 EGFR and appropriate transcription/translation regulatory components. These methods include in vitro recombinant DNA technique, DNA synthesis technique, in vivo recombinant technique and so on (Sambrook, et al. Molecular Cloning, a Laboratory Manual, Cold Spring Harbor Laboratory. New York, 1989). The DNA sequence is efficiently linked to the proper promoter in an expression vector to direct the synthesis of mRNA. The exemplary promoters are lac or trp promoter of $E.$ $coli$; $P_L$ promoter of $\lambda$ phage; eukaryotic promoter including CMV immediate early promoter, HSV thymidine kinase promoter, early and late SV40 promoter, LTRs of retrovirus and some other known promoters which control the gene expression in the prokaryotic cells, eukaryotic cells or virus. The expression vector may further comprise a ribosome-binding site for initiating the translation, transcription terminator and the like.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for $E.$ $coli$.

The vector containing said DNA sequence and proper promoter or regulatory elements can be transformed into appropriate host cells to express the protein.

The "host cell" includes prokaryote, such as bacteria; primary eukaryote, such as yeast; advanced eukaryotic, such as mammalian cells. The representative examples are bacterial cells, such as $E.$ $coli$, $Streptomyces$, $Salmonella$ $typhimurium$; fungal cells, such as yeast; plant cells; insect cells such as $Drosophila$ S2 or Sf9; animal cells such as CHO, COS or Bowes melanoma, etc.

Transcription of the polynucleotide of invention in higher eukaryotes is increased by inserting an enhancer sequence into the vector. Enhancers are cis-acting elements of DNA, usually about from 10 to 300 bp that act on a promoter to increase the gene transcription. Examples include the SV40 enhancer on the late side of the replication origin 100 to 270 bp, the polyoma enhancer on the late side of the replication origin, and adenovirus enhancers.

The skilled in the art know clearly how to select appropriate vectors, promoters, enhancers and host cells.

Recombinant transformation of host cell with the DNA sequence of invention might be carried out by conventional techniques well known to those skilled in the art. Where the host is prokaryotic such as $E.$ $coli$, the competent cells, which are capable of DNA uptake, can be prepared from cells harvested after exponential growth phase and subsequently treated by the $CaCl_2$ method using procedures well known in the art. Alternatively, $MgCl_2$ can be used. The transformation can also be carried out by electroporation, if desired. When the host is an eukaryote, such methods of transfection of DNA as calcium phosphate co-precipitates, conventional mechanical procedures such as micro-injection, electroporation, or liposome-mediated transfection may be used.

The transformants are cultured using conventional methods to express the polypeptides of the invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to conventional renaturation treatment, treatment by protein precipitant (such as salt precipitation), centrifugation, cell lysis by osmosis, sonication, supercentrifugation, molecular sieve chromatography or gel chromatography, adsorption chromatography, ion exchange chromatagraphy, HPLC, and any other liquid chromatagraphy, and the combination thereof.

The use of recombinant human de4 EGFR protein or polypeptide is versatile, which includes (but not limited to): screening of antibodies, polypeptides or other ligands activating or antagonizing de4 EGFR protein functions. Screening of polypeptide libraries by expressed recombinant human de4 EGFR protein can be used to search for therapy-valuable polypeptide molecules activating or suppressing human de4 EGFR protein functions.

On the other hand, the invention further includes the polyclonal and monoclonal antibodies possessing specificity topolypeptide ecoded from human de4 EGFR DNA or the segments thereof, especially monoclonal antibody. Herein, "specificity" means the antibody can bind to human de4 EGFR gene production or segments thereof. Preferably, it means the antibody can specifically bind to human de4 EGFR gene production or segments thereof, but can not recognize or bind to other non-related antigen molecules. In the invention, the antibodies include those binding to and inhibiting human de4 EGFR protein and further include those not affecting the protein functions of human de4 EGFR. The invention also includes the antibodies binding to the modified or unmodified human de4 EGFR gene production.

The invention not only includes intact monoclonal or polyclonal antibody, but also includes the antibody segments with immunocompetence, such as Fab' or (Fab)$_2$ segment; antibody heavy chain; antibody light chain; genetically modified single-strand Fv molecule (Ladner et al, U.S. Pat. No. 4,946, 778); or chimeric antibody, such as the antibody with mouse antibody binding specificity and still remaining part of human antibody.

The antibody of the invention can be prepared by various techniques known by the skilled in the art. For example, purified human de4 EGFR gene production or the segments thereof with antigenicity can be applied to animals to induce the generation of polyclonal antibody. Similarity, the cells expressing human de4 EGFR protein or the segments thereof with antigenicity can be used to immunize animals to produce antibody. The antibody of the invention can also be a monoclonal antibody. This kind of monoclonal antibody can be prepared by hybridoma technique (Kohler et al., *Nature* 256; 495, 1975; Kohler et al., *Eur. J. Immunol.* 6: 511, 1976; Kohler et al., *Eur. J. Immunol.* 6: 292, 1976; Hammerling et al., *In Monoclonoal Antibodies and T Cell Hybridomas*, Elsevier, N.Y., 1981). The antibody of the invention includes those which can block but not influence the protein functions of human de4 EGFR. Various antibody of the invention can be obtained by conventional immunological techniques using segments or functional regions of human de4 EGFR gene production. These segments or functional regions can be prepared by recombination method or synthesized by a polypeptide synthesizer. The antibody binding to the unmodified human de4 EGFR gene production can be produced by immunizing animals with the gene production from prokaryotic cells such as *E. Coli*; The antibody binding to the post-translational modified forms (such as glycosylated or phosphorylated proteins or polypeptides) can be produced by immunizing animals with the gene production from eukaryotic cells (such as yeast or insect cells).

The antibody against human de4 EGFR protein can be used to detect human de4 EGFR protein in biopsy specimens by immunohistochemistry.

The antibody of the invention is useful for the therapy or the prophylaxis of disorders related to the De4 EGFR protein. The appropriate amount of antibody can be administrated to stimulate or block the production or activity of De4 EGFR protein.

Antibodies can also be designed as an immunotoxin targeting at the particular site in the body. For example, a monoclonal antibody having high affinity to De4 EGFR protein can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill De4 EGFR protein-positive cells.

The polyclonal antibodies can be prepared by immunizing animals, such as rabbit, mouse, and rat, with De4 EGFR protein. Various adjuvants, e.g., Freund's adjuvant, can be used to enhance the immunization.

By using the antibody of the invention, through various traditional screening methods, the materials interacting with de4 EGFR protein can be screened, such as receptors, inhibitors, agonists or antagonists etc.

Different effects can be obtained when the protein of the invention and antibody, inhibitors, agonists, antagonists or receptors thereof are administrated (as drugs) in therapy. Usually, these substances can be prepared in non-toxic, inert and pharmaceutically acceptable aqueous carriers, wherein pH value is usually about 5-8, and preferably about 6-8, though pH value can be altered due to the change of preparation substance and diseases to be treated. Prepared pharmaceutical composition can be administrated in conventional ways, including (but not limited to): inside tumor, inside muscle, inside abdominal membrane, inside vein, under skin, inside skin or partial administration.

The antibody against de4 EGFR protein of the invention can be used for disease treatment, such as inhibiting tumor cell invasion or migration. Other reagents for therapy can be used at the same time of using of the antibody of the invention, such as anti-tumor chemotherapeutic reagent and so on.

The invention further provides a pharmaceutical composition containing a safe and effective dosage of de4 EGFR polypeptide of the invention or the agonists thereof, antagonists thereof and pharmaceutically acceptable carriers or excipients. This kind of carriers includes (but not limited to): salt water, buffer, glucose, water, glycerol, alcohol, and the mixture thereof. Pharmaceutical formulation should match administration method. The pharmaceutical composition of the invention can be produced in the form of ampul, for example, it can be prepared with saline or aqueous solution containing glucose and other adjuvants by conventional methods. The pharmaceutical composition such as tablet and capsules can be prepared through conventional methods. The pharmaceutical composition such as ampuls, solutions, tablets and capsules should be prepared under sterile conditions. The administrated quantity of active ingredient is the effective dose for therapy, for example, 1 µg/kg weight-5 mg/kg weight per day. Additionally, the polypeptide of the invention can be used in conjunction with other therapeutic agents.

Use of a pharmaceutical composition means administrating mammals with the safe and effective dosage of de4 EGFR antagonists. Usually, the safe and effective dosage is at least 10 µg/kg weight, and mostly does not exceed 8 mg/kg weight, more preferably about 10 µg/kg weight-about 1 mg/kg weight. Of course, the specific dose should be considered according to the administration and patient health, which are well-known by the skilled physicians.

Also included in the invention are ribozyme and the oligonucleotides, including antisense RNA and DNA, which inhibit the translation of De4 EGFR mRNA. Ribozyme is an enzyme-like molecule capable of specifically cutting certain RNA. The mechanism is the nucleic acid endo-cleavage after the specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and in the downstream of RNA polymerase promoter. In order to increase stability, the nucleic acid molecules can be modified in many manners, e.g., increasing the length of the flanking sequences, replacing the phosphodiester bond with the phosphothioester bond in the oligonucleotide.

The methods for introducing the polynucleotides into tissues or cells include: directly injecting the polynucleotides into tissue in the body, in vitro introducing the polynucleotides into cells with vectors, such as virus, phage, or plasmid, and then transplanting the cells into the body.

Polypeptide molecules, which can be bound to human de4 EGFR protein, can be obtained by screening the random polypeptide library consisted of amino acids potentially to be combined bound to solid phase material. During the screening, human de4 EGFR protein must be labeled.

The invention also relates the diagnosis method for detecting human de4 EGFR protein level quantitatively and directionally, which are well-known in the art and include FISH test and radioimmunoassay. The protein level of human de4 EGFR to be tested in the trial can be used to explain the importance of human de4 EGFR protein in various diseases and diagnose the diseases which de4 EGFR effected.

One method for detecting the presence of de4 EGFR protein in samples is to use the specific antibody of de4 EGFR protein, which includes: contact the specific antibody with the samples; observe the formation of antibody complex, and the formation of antibody indicates that de4 EGFR protein is present in the samples.

The polynucleotide encoding De4 EGFR protein can be used in the diagnosis and treatment of De4 EGFR protein related diseases. The polynucleotide encoding De4 EGFR can be used to detect whether De4 EGFR is expressed or not, and whether the expression of De4 EGFR is normal or abnormal, e.g., in the case of diseases. De4 EGFR DNA sequences can be used in the hybridization with biopsy samples to determine the expression of De4 EGFR. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analysis the differential expression of genes in tissues and for the diagnosis of genes. The De4 EGFR specific primers can be used in RNA-polymerase chain reaction and in vitro amplification to detect the transcripts of De4 EGFR Further, detection of the mutation of De4 EGFR gene is useful for the diagnosis of De4 EGFR protein related diseases. The mutation forms of De4 EGFR include site mutation, translocation, deletion, rearrangement and any other mutations compared with the wild-type De4 EGFR DNA sequence. The conventional methods, such as Southern blotting, DNA sequencing, PCR and in situ blotting, can be used to detect mutation. Moreover, mutation sometimes affects the expression of protein. Therefore, Northern blotting and Western blotting can be used to indirectly determine whether the gene is mutated or not.

The sequences of the present invention are also valuable for chromosome identification. In brief, sequences can be mapped to chromosomes by preparing PCR primers (preferably 15-35 bp) from the cDNA of de4 EGFR of the invention. These primers are then used for PCR screening of somatic cell hybrids containing individual human chromosomes. Only the cell hybrids, which contain the genes corresponding to the primers, produce amplified fragments.

Once a sequence has been mapped to a precise chromosomal location, the physical position of the sequence on the chromosome can be correlated with genetic map data. Such data are found in, e.g., Mendelian Inheritance in Man (available on-line through Johns Hopkins University Welch Medical Library). The relationships between genes and diseases that have been mapped to the same chromosomal region are then identified through linkage analysis.

In one embodiment of the invention, an isolated polynucleotide is provided, which encoding polypeptide with amino acid sequence of SEQ ID NO: 2. The sequence of the polynucleotide is shown as SEQ ID NO: 1, wherein the full length of polynucleotide sequence is 3498 base pairs, with the ORF is located at No. 1-3495, which encoding human de4 EGFR with 1165 amino acids (SEQ ID NO: 2).

The present invention will be further illustrated below with references to the specific examples. It should be understood that these examples are only to illustrate the invention but not to limit the scope of the invention. The experimental methods with no specific conditions described in the following examples are generally performed under the conventional conditions such as Sambrook et al., Molecular Cloning: A Laboratory Manual (New York: Cold Spring Harbor Laboratory Press, 1989), or according to the manufacture's instructions. Unless indicated otherwise, parts and percentage are calculated by weight.

EXAMPLE 1 de4 EGFR Sequence and the Expression thereof Obtained by PCR

Experimental Materials

Hepatocellular carcinoma cell line HepG2 and Hep3B were purchased from ATCC; Huh7, 7402, 7405, 7703, 7404 and 7721 were purchased from Chinese Academy of Science; human monocytic tumor cell line U937 was purchased from ATCC; cervical cancer cell line C33A and Hela were purchased from ATCC; breast cancer cell line MCF-7 and SK-BR-3 were purchased from ATCC; ovarian cancer cell line Skov3 and CaoV3 were purchased from ATCC; OMC685 was purchased from Zunyi school of medicine; lung cancer cell line A549, H460 and H1299 were purchased from ATCC, spcA1 was purchased from Chinese Academy of Science.

The origin of 19 hepatocellular carcinoma tissues and the corresponding adjacent noncancerous tissues: Qidong Liver Cancer Institute The origin of 10 ovarian cancer tissues: Shanghai Ninth People's Hospital The orgin of 18 prostate cancer tissues: Shanghai Changhai Hospital Ten normal tissue RNAs were purchased from Clontech Company The RNA extraction reagent Trizol was purchased from Invitrogen Company Reverse transcriptase and reverse transcription kit were purchased from Promega Company Taq polymerase for PCR short-strand amplification was purchased from Shanghai Biocolor BioScience and Technology Company. LA Taq polymerase for PCR long-strand amplification was purchased from TAKARA Company.

All the primers were synthesized by Invitrogen Company

The acquisition of all the tissues had Informed Consent. The research was reviewed and approved by the related Institutional Ethics Review Committee.

Experimental Methods

Total RNA was extracted from the cells or tissues by Trizol reagent. The cDNA was obtained by reverse transcription. The partial specific sequence and full length of EGFR and the isoform thereof was amplified by nested PCR. The used primers was listed as below:

```
de4 EGFR gene sequence short-strand amplification:
outside primers (5' to 3')
                                        (SEQ ID NO: 3)
EJC-V3P1: GTATTGATCGGGAGAGCCG
                                        (SEQ ID NO: 4)
EJC-V3P2: GTGGAGATCGCCACTGATG amplification conditions: 1 cycle: 94° C. 5 min
   28 cycles: 94° C. 1 min; 58° C. 1 min; 72° C.
   1 min
   1 cycle: 72° C. 10 min inside primers
                                        (SEQ ID NO: 5)
de4 EGFR sf: CCCATGAGAAATTTACAGGGC
                                        (SEQ ID NO: 6)
EGFR QR2: GTGGTGGGGTTGTAGAGCATG amplification conditions: 1 cycle: 94° C. 5 min
   28 cycles: 94° C. 30 sec; 60° C. 30 sec;
   72° C. 30 sec;
   1 cycle: 72° C. 10 min de4 EGFR gene sequence long-strand amplification:
outside primers
```

-continued

```
                                          (SEQ ID NO: 7)
upstream: EJC-V3P1: GTATTGATCGGGAGAGCCG
                                          (SEQ ID NO: 8)
downstream: ER-28wtR1: TGACTTGATACAGTACCGATCCGG amplification conditions: 1 cycle: 94° C. 5 min
   28 cycles: 94° C. 1 min; 58° C. 2 min; 72° C.
   4 min
   1 cycle: 72° C. 10 min inside primers
                                          (SEQ ID NO: 9)
upstream: de4 EGFR sf: CCCATGAGAAATTTACAGGGC
                                         (SEQ ID NO: 10)
downstream: ER-28wtR1: TGACTTGATACAGTACCGATCCGG
or
                                         (SEQ ID NO: 11)
ERiso26R2: CAACAGAGGTACAGCAAACAACCAG amplification conditions: 1 cycle: 94° C. 5 min
   30 cycles: 94° C. 1 min; 60° C. 2 min; 72° C.
   4 min
   1 cycle: 72° C. 10 min EGFRwt gene sequence short-strand amplification:
outside primers
                                         (SEQ ID NO: 12)
EJC-V3P1: GTATTGATCGGGAGAGCCG
                                         (SEQ ID NO: 13)
EJC-V3P2: GTGGAGATCGCCACTGATG amplification conditions: 1 cycle: 94° C. 5 min
   28 cycles: 94° C. 1 min; 58° C. 1 min; 72° C.
   1 min
   1 cycle: 72° C. 10 min inside primers
                                         (SEQ ID NO: 14)
upstream: ERE4F: catccagtggcgggacatag
                                         (SEQ ID NO: 15)
downstream: EGFR QR2: GTGGTGGGGTTGTAGAGCATG amplification conditions: 1 cycle: 94° C. 5 min
   28 cycles: 94° C. 30 sec; 60° C. 30 sec;
   72° C. 30 sec;
   1 cycle: 72° C. 10 min EGFRwt gene sequence full-length amplification:
outside primers
                                         (SEQ ID NO: 16)
upstream: EJC-V3P1: GTATTGATCGGGAGAGCCG
                                         (SEQ ID NO: 17)
downstream: ER-28wtR1: TGACTTGATACAGTACCGATCCGG amplification conditions: 1 cycle: 94° C. 5 min
   28 cycles: 94° C. 1 min; 58° C. 2 min; 72° C.
   4 min
   1 cycle: 72° C. 10 min inside primers
                                         (SEQ ID NO: 18)
upstream: V3F: ATGCGACCCTCCGGGACG
                                         (SEQ ID NO: 19)
downstream: ERwt28R2: GGAATCAAGCATCCTCTGGAAGAC amplification conditions: 1 cycle: 94° C. 5 min
   30 cycles: 94° C. 1 min; 60° C. 2 min; 72° C.
   4 min
   1 cycle: 72° C. 10 min
```

Experimental Results

Figure 2:
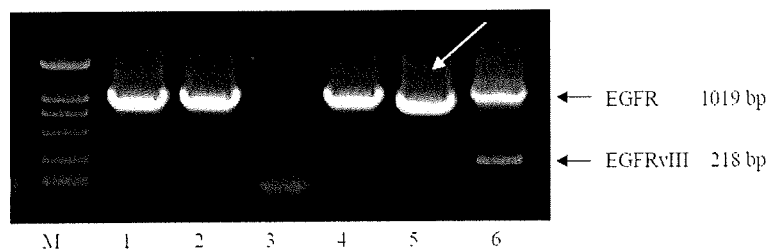
FIG. 2 shows the electrophoretogram of de4-EGFR. The lanes in the figure represent as following: 1. 7402; 2. 705; 3. 7703; 4. HepG3B; 5. SKOV3; 7. 7404.

At first, an amplified band slightly smaller than wild-type EGFR was detected in SKOV3 cells by RT-PCR (primers: EJC-V3P1/EGFR QR2) (FIG. 2). Sequencing analysis demonstrated that in comparison to wild-type EGFR, it lost the whole exon 4 with the length of I 58 bp. So it was named as de4 EGFR.

Figure 3:
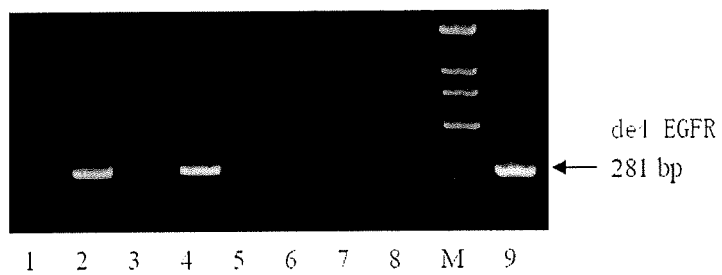
FIG. 3 shows the presence of de4-EGFR in partial ovarian cancer tissues. In the figure, lanes 1-9 represent different ovarian cancer tissues.

Then, design and synthesize primers specific to de4 EGFR, and conduct the RT-PCR in tissue samples (primers: EJC-V3PI/EGFR QR2). De4 EGFR gene expression was detected in 3 of 9 ovarian cancer tissues (FIG. 3).

Figure 4:
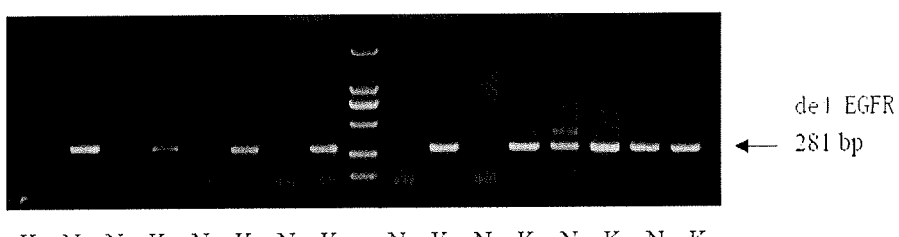
FIG. 4 shows the presence of de4-EGFR in partial hepatocellular carcinoma tissues.
Figure 5:
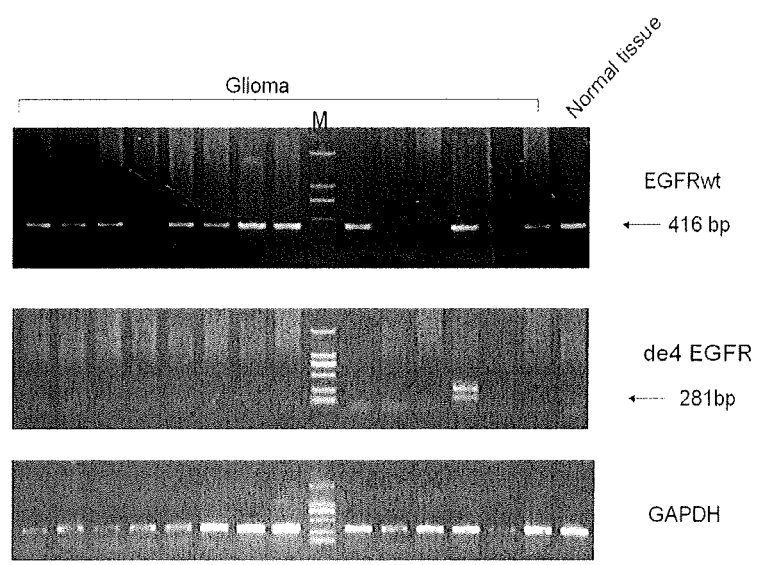
FIG. 5 shows the presence of de4-EGFR in partial gliomas tissues.

Of 20 cancerous tissues and corresponding adjacent non-cancerous tissues, De4 EGFR gene expression was detected in 7 cancerous tissues and 3 corresponding adjacent noncancerous tissues (FIG. 4). de4 EGFR is expressed in 1 of 14 brain gliomas tissues. (FIG. 5)

Figure 6:
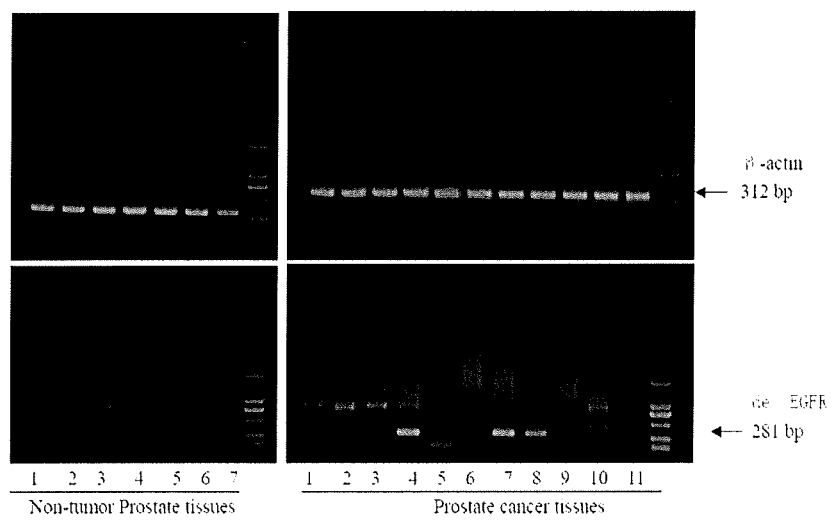
FIG. 6 shows the presence of de4-EGFR in prostate cancer tissues. In the figure, lanes 1-11 represent different prostate cancer tissues.

De4 EGFR gene expression was not detected in 7 noncancerous prostate tissues, and was detected in 3 of 11 cancerous prostate tissues (FIG. 6).

Figure 7:
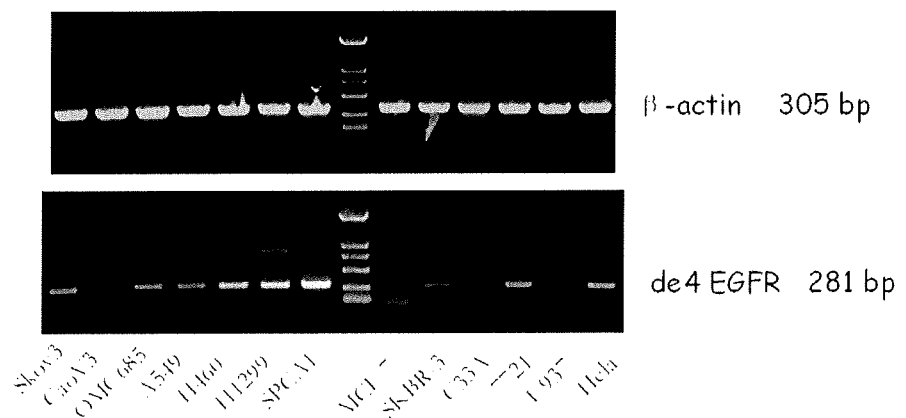
FIG. 7 shows the expression of de4 EGFR in different cancer cell lines.

Furthermore, de4 EGFR gene expression was detected in various cell lines: epithelial carcinoma cell line A431, cervical cancer cell line Hela, breast cancer cell line MDA-MB-468, MCF-7, SK-BR-3, ovarian cancer cell line OMC685, lung carcinoma cell line A549, H460, H1299, SPCA1 and hepatocellular carcinoma cell line 7721 (FIG. 7).

The above results indicated that there was a certain universality, which in the previous literature has not yet been reported.

Figure 8:
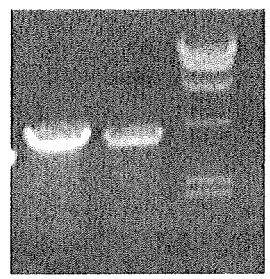
FIG. 8 shows the amplification of de4 EGFR by long-strand primers. The lanes represent as following: 1. Hela; 2. hepatocellular carcinoma tissues K416.

It is well known that there are many types of deletion mutants and site mutants of EGFR in various cancer cells and tissues. To test the DNA sequence difference between long-strand de4 EGFR and wt EGFR, the inventor decides to amplify long-strand de4 EGFR and conduct the sequencing. The long-strand DNA of de4 EGFR was amplified in Hela cell and one hepatocellular carcinoma tissue with the template of cell and tissue cDNA and primers designed according to human EGFR sequence from GeneBank (FIG. 8).

The DNA sequencing results showed that in comparison to wild-type EGFR, de4 EGFR lost the whole sequence of exon 4.

Figure 9:
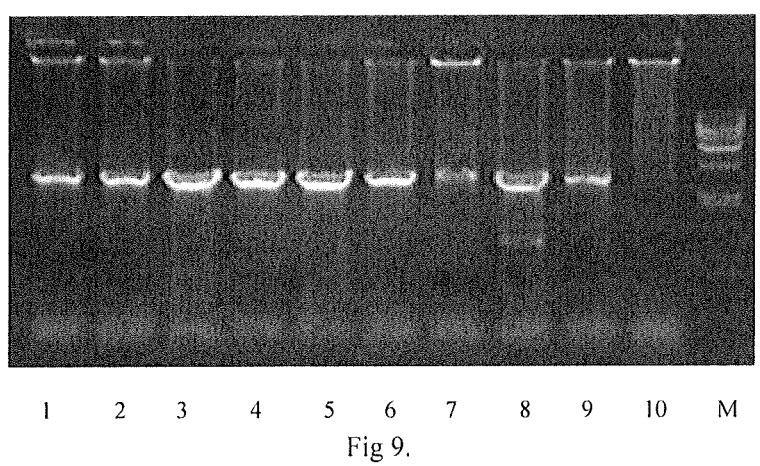
FIG. 9 shows the test result of EGFR wt mRNA in normal tissues. The lanes represent as following: 1: brain; 2: colon; 3: kidney; 4: liver; 5: lung; 6: ovary; 7: pancreas; 8: placent; 9: spleen; 10: stomach.

In addition, the gene expression of de4 EGFR was detected in normal tissues. The mRNA level detection of EGFR wt and de4 EGFR in 10 normal human tissues (Clontech) indicated: at mRNA levels, EGFR wt was expressed at different levels in 10 normal tissues (FIG. 9). In contrast, de4 EGFR gene expression was not found in normal tissues.

EXAMPLE 2

Establishment of Cell Lines Expressing EGFR and the Mutant thereof

Experimental Materials:

Cell lines: 293T cell was purchased from Chinese Academy of Science, NIH-3T3 cell was purchased from ATCC, U87MG cell was purchased from ATCC.

Plasmids: pWPT-GFP, psPAX2 and pMD2G lentiviral vectors were purchased from ADDGENE INC. (USA).

The sequences of EGFR wt and de4 EGFR were amplified respectively. After DNA sequencing, GFP was replaced by pWPT-GFP, thus pWPT-EGFR wt and pWPT-de4 EGFR were generated. pWPT-EGFR wt or pWPT-de4 EGFR was introduced into 293T cells (Chinese Academy of Science, shanghai, China) respectively with packaging plasmid psPAX2 and G-protein of vesicular stomatitis virus (VSV-G) envelope plasmid pMD2.G (purchased from Addgene Company) using a calcium phosphate transfection system. NIH/3T3 cells and U87MG cells ($1 \times 10^5$) were infected by virus, and 6 μg/mL Polybrene (Sigma Chemical, USA) was added during the infection. After identification of the mixed clones by Western blot, 100 cells were seeded in the plates. Six monoclones were selected and conduct identification by Western blot. The clones with consistent expression were selected for further experiments.

Experimental Method:

Lentivirus enveloping: 20 μg Transfer vector, 6 μg Envelope plasmid pMD2G and 15 μg packaging plasmid psPAX2 were introduced into viral packaging cell 293T by calcium phosphate transfection system. NIH-3T3, U87MG and 293 cells were infected by the produced viral particles.

Experimental Results

Figure 10:
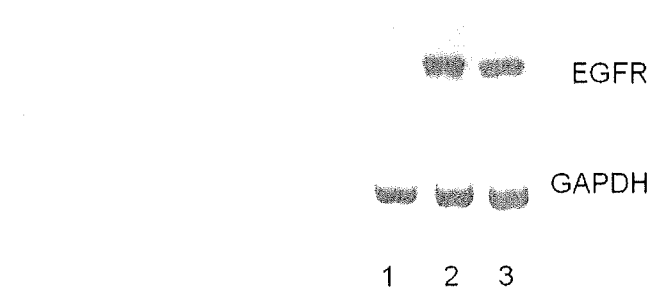
FIG. 10 shows the establishment of NIH3T3-related cell model by Western blot detection. The lanes in the figure represent as following: 1. NIH3T3 GFP; 2. NIH3T3 EGFR wt; 3. NIH3T3 de4 EGFR.
Figure 11:
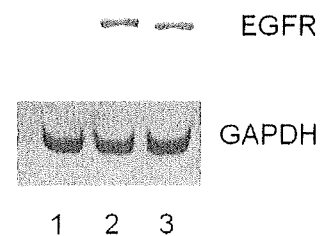
FIG. 11 shows the establishment of U87-related cell model by Western blot detection. The lanes in the figure represent as following: 1. U87 GFP; 2. U87 EGFR wt; 3. U87 de4 EGFR.

The high expressing cell lines of EGFR and the mutants thereof was established in mouse fibroblast cell line NIH3T3 and glioma cell line U87MG, which was verified by Western blot (FIGS. 10 and 11).

EXAMPLE 3

EGFR and the Mutants thereof Promote Cells Proliferation and Migration in vitro

Experimental Materials:

3T3 cell line was purchased from ATCC. CCK-8 kit was purchased from Dojindo Laboratories Transwell chamber (pore size: 8.0 μm) and matrigel were purchased from BD Bioscience Company.

Experimental Method:

(a) Cell growth curve assay: Cells were digested and counted, seeded in a 96-well plate, 300 cells per well. Five repeated samples were seeded. Absorbance was tested at 450 nm using a CCK-8 kit every 24 hours in successive 7 days.

(b) Transwell migration assay: To precisely detect the function of de4 EGFR in cell migration, transwell migration assay was performed. Then $5\times10^4$ cells were suspended in 200 μL serum-free medium and then added to the transwell upper chambers, 600 μL medium containing 10% FBS was added to the lower chambers. After being cultured for 12 h (NIH3T3 GFP, NIH3T3 EGFR wt, NIH3T3 de4 EGFR) or 24 h (U87MG GFP, U87MG EGFR wt, U87MG de4 EGFR), the cells were fixed for 1 h by 4% paraformaldehyde. The non-migrated cells in upper chambers were scraped with cotton swabs, and the cells were stained with 1% crystal violet for 30 min. The migrated cells were pictured microscopically (100× amplification) and counted.

(c) Transwell invasion assay: To detect the function of de4 EGFR in cell invasion, transwell cell invasion assay was performed. In the transwell upper chambers were paved 100 μL 1 μg/μL Matrigel, incubated at 37° C. for 4 h. The Matrigel was then washed with the serum-free medium twice. Count $1\times10^5$ cells, which were suspended in 200 μL serum-free medium and then were added to the upper chambers paved with Matrigel. 600 μL medium containing 10% FBS was added to the lower chambers. After being cultured for 24 h, the cells were fixed by 4% paraformaldehyde for 1 h. The non-migrated cells in upper chambers were scraped with cotton swabs and the cells were stained with 1% crystal violet for 30 min. The migrated cells were pictured microscopically (100× amplification) and counted.

Figure 12:
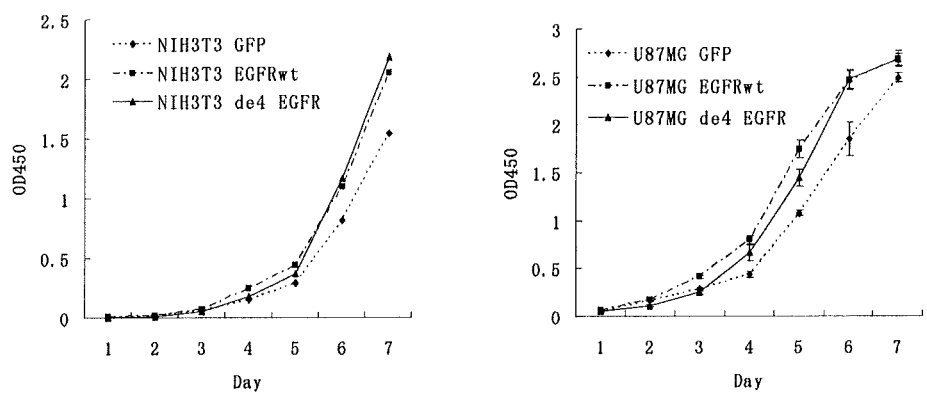
FIG. 12 shows that EGFR and the mutant thereof can promote cell proliferation.

Experiment Results:

The growth curve was showed in FIG. 12. The results indicated that EGFR and the mutant thereof obviously promote cell proliferation. From day 6, compared with control cells U87MG GFP, EGFR-WT and de4 EGFR over-expressing U87MG have more activity of cell proliferation (p<0.01). However, there was no significant difference between U87MG EGFR-WT and U87MG de4 EGFR in cell proliferation (p>0.05). The similar results were obtained in NIH3T3 cells.

Figure 13:
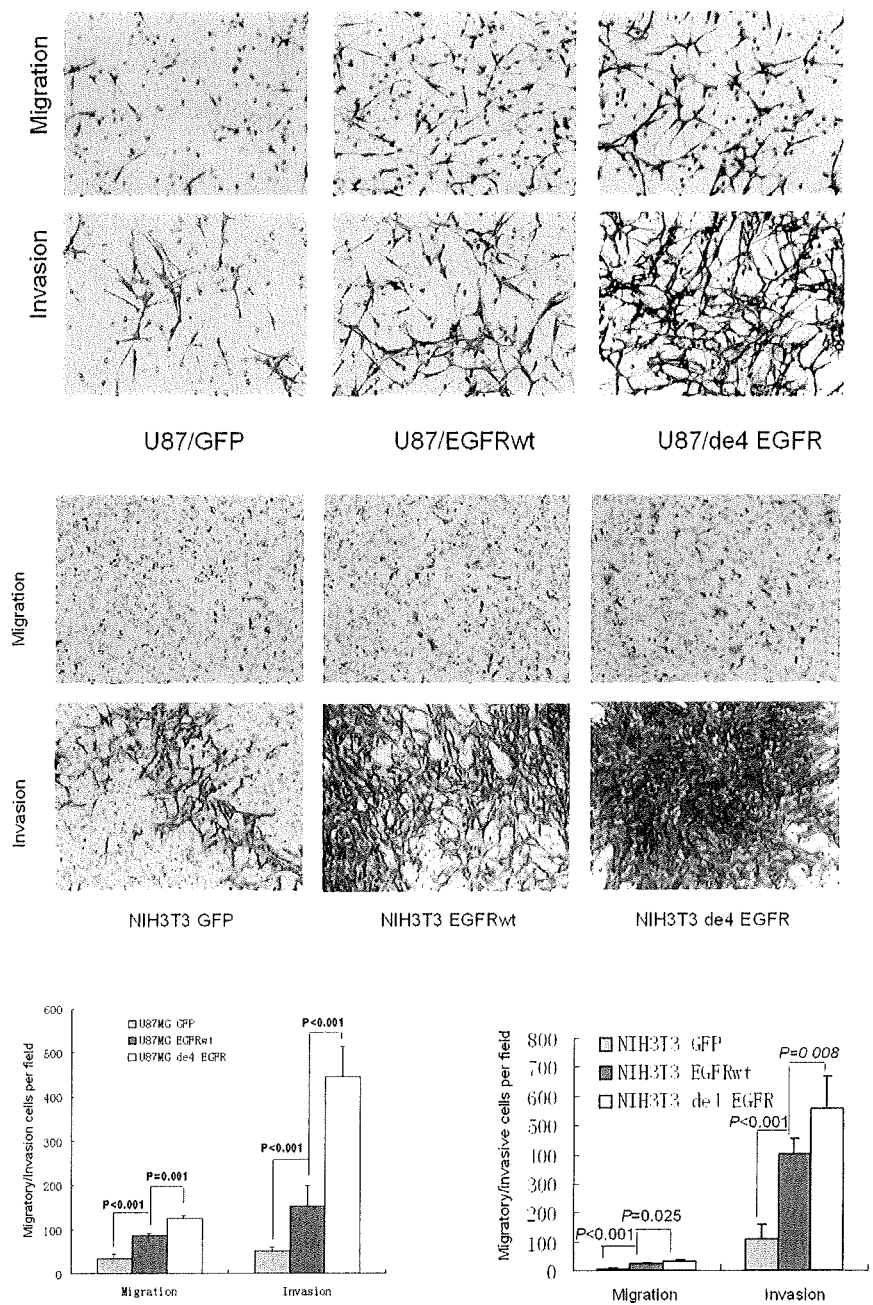
FIG. 13 shows that EGFR and the mutant thereof can promote cell migration.

The transwell cell migration and invasion assay showed more obvious result which is that de4 EGFR promotes cell migration and invasion more significantly than EGFR-WT in both mouse fibroblast cell line NIH3T3 and human glioma cell line U87MG (FIG. 13).

EXAMPLE 4

EGFR and the Mutant thereof Promote Cell Proliferation in vivo

Experimental Method:

The 6-8 weeks-old nude mice were separated into three groups, five per group. U87MG GFP, U87MG EGFR wt and U87MG de4 EGFR were injected into the right hind flank of each mice in three groups in the amount of $1\times10^6$ cells. The tumor volume and weight were measured after 26 days. The used analysis software was SPSS11.0. The equality of the variances between each group was analyzed by lenvene test, and then the significant difference in total was testified by variance analysis. At last, the comparison between each group was operated by LSD method.

Figure 14:
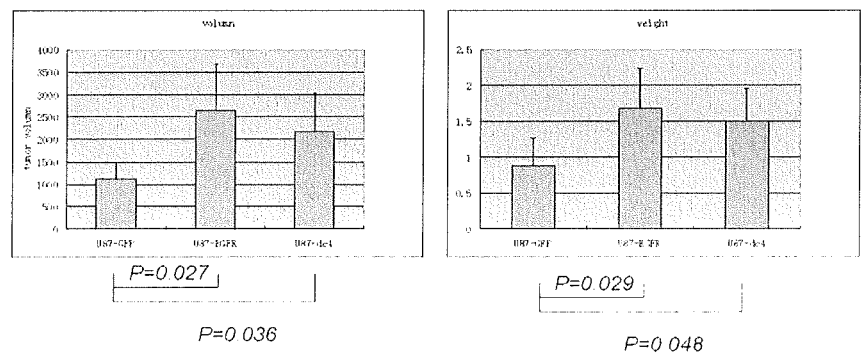
FIG. 14 shows that EGFR and the mutant thereof can promote tumor cell proliferation in vivo.

Experimental Result:

According to the detection of tumor volume and weight (FIG. 14), compared with the control cells, U87MG EGFR wt (P=0.027 (tumor volume), P=0.029 (tumor weight)) and U87MG de4 EGFR (P=0.036 (tumor volume), P=0.048 (tumor weight)) cells have strong ability of tumorigenesis. On the other hand, there was no significant difference between U87MG EGFR wt and U87MG de4 EGFR in tumorigenesis (P>0.05).

EXAMPLE 5

EGFR and the Mutant thereof Promote Cell Migration in vivo

Experimental Method:

The 6-8 weeks-old nude mice were separated into three groups, eight per group. U87MG GFP, U87MG EGFR wt and U87MG de4 EGFR were injected into the right hind flank of each mice in three groups in the amount of $1\times10^6$ cells. If the tumor has strong ability of invasion, metastases will occur outside the original position (right hind flank). The mice were sacrificed after week 8, weight the lung and the tissues were subjected to immunohistochemistry. The used analysis software was SPSS11.0. The equality of the variances between each group was analyzed by lenvene test, and then the significant difference in total was testified by variance analysis. At last, the comparison between each group was operated by LSD method.

Figure 15:
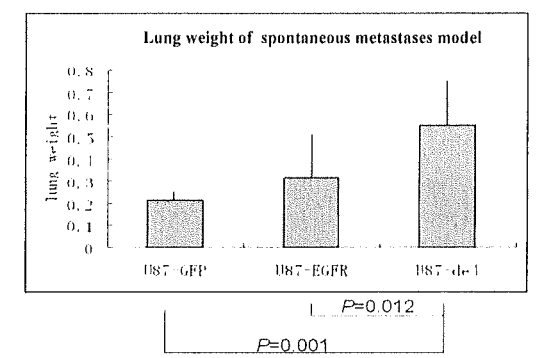
FIG. 15 shows that EGFR and the mutant thereof can promote tumor cell migration and metastasis in vivo.
Figure 15:
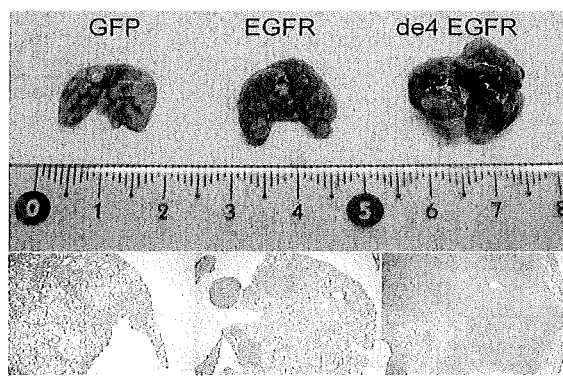

Experimental Result:

As shown in FIG. 15, compared with wild-type EGFR, de4 EGFR promotes tumor metastases more significantly, which was revealed by the difference of mice lung weight. Nodules were found occasionally in mice lung injected with U87MG GFP and U87MG EGFR wt cells, and basic state of lung was maintained. However, many nodules were found in mice lung injected with U87MG de4 EGFR cells. The lung weight of mice inoculated with U87MG de4 EGFR group significantly exceeded that of U87MG GFP (P=0.001) and U87MG EGFR wt (P=0.012) groups. Through observation, comparison and immunohistochemistry detection, the degree of tumor invasion in mice lung from low to high was GFP group, EGFR wt group and de4 EGFR group.

Figure 16:
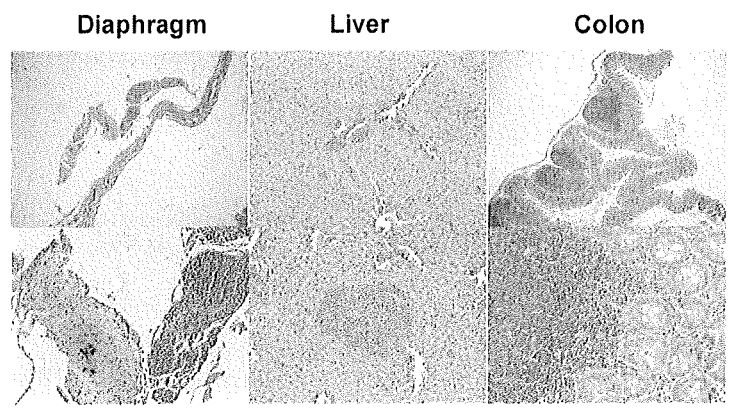
FIG. 16 shows de4 EGFR can promote tumor cell multiple metastases in vivo.

More importantly, among the 8 mice inoculated with de4 EGFR, extrapulmonary distal metastases appeared in 2 mice, and the metastasis was in liver, diaphragm and colon (FIG. 16). No extrapulmonary distal metastases in GFP and EGFR groups were observed.

The results above strongly indicated that de4 EGFR mutant promotes tumor migration and invasion more significantly than EGFR wt.

EXAMPLE 6

Preparation of Monoclonal Antibody Recognizing de4 EGFR or EGFR wt

Polypeptides corresponding to EGFR wt intracellular and Polypeptides corresponding to de4 EGFR extracellular region were synthesized respectively. The polypeptide sequences were CSTAENAEYLRVAPQSSEFIGA (EGFR wt) (SEQ ID NO: 20) and NLQGQKC (de4 EGFR) (SEQ ID NO: 21). Then the polypeptides were conjugated to maleimide-activated keyhole limpet hemocyanin (KLH) in a 1:1 mass ratio. The mice were immunized by 100 μg polypeptide-KLH in Freund's complete adjuvant in a 1:1 ratio. After four weeks, the mice were immunized by 100 μg polypeptide-KLH in Freund's incomplete adjuvant in a 1:1 ratio. The immunization was repeated once after two weeks. The monoclonal antibodies were screened by traditional hybridoma technique and their specificity was verified with EGFR wt and de4 EGFR stably expressed cell lines. These antibodies can be used for detection of EGFR wt and de4 EGFR in ELISA, Western blot (WB), immunofluorescence (IF) and immunohistochemistry (IHC).

As the result, a monoclonal antibody 1F8 specifically recognizing de4 EGFR and a monoclonal antibody 1C5 specifically recognizing EGFR wt were obtained.

EXAMPLE 7

Expression and Purification of de4 EGFR Recombinant Protein

The NIH3T3-de4 EGFR-positive clones were selected and cultured for expansion, and monolayer cells were washed twice with cold phosphate buffer at pH7.4, added with buffer A (2% Triton X-100, 100 mM NaCl, 50 mM Hepes, 1 mM EGTA, 0.5 μg/ml Leupetin, 20 μM pmsf pH=7.4) and cooled on ice for 15 min. monolayer cells were scraped and centrifuged at 10000 g for 5 min at 4° C. The supernatant were collected and filtered with 0.22 mm membrane, then added to the CNBr-activated Sepharose 4B affinity chromatography column with the antibody 1F8 recognizing de4 EGFR. The column was completely washed with buffer B (0.5% Triton X-100, 100 mM NaCl, 50 mM Hepes, 20 μM pmsf, 1 mM EGTA, pH=7.4) and eluted with buffer C (0.5% Triton X-100, 100 mM NaCl, 100 mM Citrate, 20 μM pmsf, 1 mM EGTA, pH=3.0). The eluent was collected and neutralized by 1M Tris Hcl (pH=9.6) in 1/10 volume of it, Human de4 EGFR protein was obtained.

EXAMPLE 8

Production of Antibody Against de4 EGFR Protein

The recombinant human de4 EGFR proteins obtained in example 7 were used to immunize animals to produce antibody. The detailed method was described below. Recombinant molecular was stored after purification by chromatography, which could also be separated by SDS-PAGE. The band was cut from gel and emulsified with Freund's complete adjuvant with equivalent volume. 50-100 μg/0.2 ml emulsified proteins were intraperitoneally injected to mice. After 14 days, the same antigens emulsified with Freund's incomplete adjuvant were intraperitoneally injected to mice at 50-100 μg/0.2 ml to enhance immunization. The enhancing immunization was repeated every 14 days for at least three times. The specific reaction activity of obtained antiserum was estimated by the ability to immunoprecipitate human de4 EGFR translated products in vitro. The results showed that the antibody could specifically bind to the protein of the invention.

EXAMPLE 9

Screening of Antagonist for de4 EGFR Polypeptides

According to the transwell migration assay described in example 3, add the two reagents as below to U87-de4 EGFR cell line: (a) candidate (b) blank control, and observe the affection on cell migration.

If the cell migration of group (a) was significantly lower than that of group (b) statistically, it indicated that this candidate reagent was the antagonist for de4 EGFR polypeptides; if it was significantly higher than that of group (b), it indicated that this candidate regent was the agonist for de4 EGFR polypeptides. Similarly, according to the transwell invasion assay described in example 8, add the two reagents as below to MDA-MB-468 cell (expressing de4 EGFR): (a) candidate (b) blank control, and observe the affection on cell invasion.

If the cell invasion of group (a) was significantly lower than that of group (b) statistically, it indicated that this candidate reagent was the antagonist for de4 EGFR polypeptides; if it was significantly higher than that of group (b), it indicated that this candidate regent was the agonist for de4 EGFR polypeptides.

Result:
Several candidates were tested, including antibody C225 (Erbitux, cetuximab) (purchased from Merck company, Germany) and CH12 antibody (preparation according to Chinese patent application No200810038848.8, PCT patent application number: PCT/CN2009/074090). The results indicated that antibody CH12 could significantly inhibit cell migration and invasion of de4 EGFR cells.

EXAMPLE 10

Therapy Experiments in vitro and in vivo

Experimental Materials:
CCK-8 kit was purchased from Dojindo Laboratories. Experimental antibody C225 (Erbitux, cetuximab) was from Germany Merck Company; CH12 antibody was prepared by the inventor according to the method in Chinese patent application No 200810038848.8.

The 6-weeks-old female nude mice were selected for experiment. They were provided by Shanghai Cancer Institute.

Experimental Methods:
Antibody therapy experiment in vitro:
U87MG de4 EGFR cells were counted after digestion. Then the cells were seeded in a 96-well plate, $4 \times 10^4$ cells per well. Five repeated samples were set. When the cell confluence was 40%, administrate the antibody at final concentration of 0, 2, 20, 40, 100 and 250 μg/ml respectively. After 72 hours, the absorbance at 450 nm was tested by CCK-8 kit.

Inhibition rate equation:

Inhibition rate=
[(OD$_{450(average\ in\ the\ wells\ without\ antibody)}$−
OD$_{450(average\ in\ the\ wells\ with\ antibody\ at\ certain\ concentration)}$]/
OD$_{450(average\ in\ the\ wells\ without\ antibody)}$]×100%

Antibody Therapy Experiment in vivo

The 6-8 weeks-old nude mice were separated into three groups, seven ones per group. 5×10$^5$ U87MG de4 EGFR cells were injected into the right hind flank of each mice in three groups. Start the therapy after 5 days, intraperitoneally administrate C225 and CH12 antibody into mice at dose of 0.5 mg/mouse/time respectively, and PBS was set as control. The antibodies were administrated every two days and tumor volume was measured. After 6 days, the therapy was stopped. Keeping observation for 2 weeks, then the experiment was stopped. The mice was sacrificed and the weight of tumor tissues were measured and recorded.

Inhibition rate equation:

Inhibition rate=[(average tumor weight of PBS therapy group−average tumor weight of antibody therapy group)/average tumor weight of PBS therapy group]×100%

Experimental Results

1. Antibody therapy experiment in vitro

Figure 17:
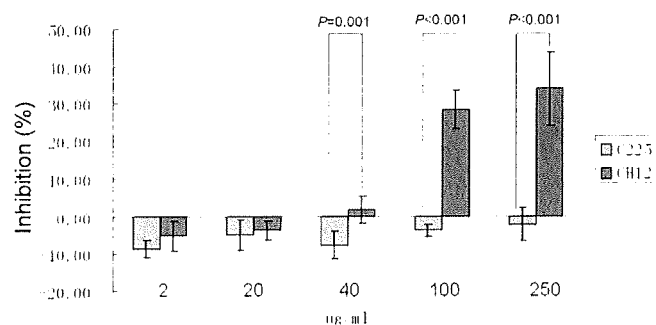
FIG. 17 shows the inhibition of antibodies CH12 and C225 to the proliferation of U87MG de4 EGFR cell in vitro.

As shown in FIG. 17, when the concentration of antibody exceeded 100 μg/ml, the inhibiting effect on cell proliferation of CH12 antibody was obviously better than that of C225 antibody. The inhibition rate of CH12 was 30%-40%. In contrast, therapy effect of C225 was not observed. When the concentration of antibody was lower than 40 μg/ml, both of them had no obvious inhibiting effects.

2. Antibody therapy experiment in vivo

Figure 18:
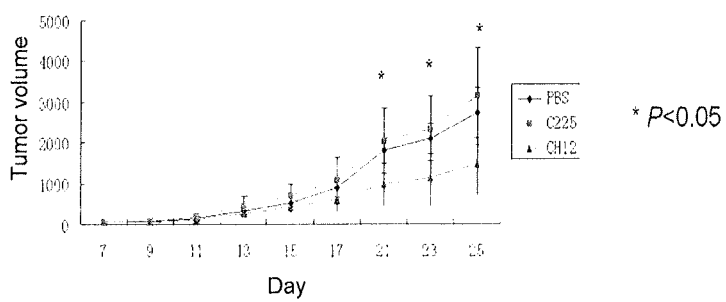
FIG. 18 shows the inhibition of antibodies CH12 and C225 to the proliferation of U87MG de4 EGFR cell in vivo.

As shown in FIG. 18, in view of the change of tumor volume in vivo, after cell inoculation for 21 days, compared with PBS control group, different CH12 antibody therapy groups showed obvious therapy effects (*: P<0.05). In contrast, C225 had no inhibiting effects on U87 de4 EGFR cell growth in mice.

Figure 19:
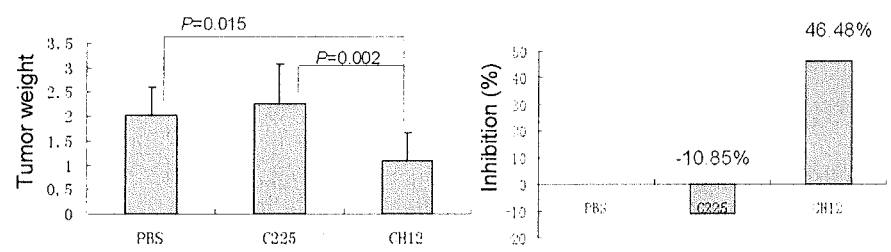
FIG. 19 shows the tumor weight and inhibition rate analysis after the treatment of U87MG de4 EGFR by CH12 and C225 in vivo.

The record of tumor weight presented in FIG. 19 showed similar tendency: in view of tumor weight, inhibition rate of tumor growth was 46.48% for CH12 group in comparison to PBS group. However, C225 didn't show inhibiting effects and even displayed slight activation of tumor cell growth.

The results above indicated that in vitro and in vivo, compared with C225 antibody, CH12 antibody has better tumor inhibiting effects on de4 EGFR over-expressed U87MG cells.

Discussion

The de4 EGFR of the invention is a new variant of EGFR, with a deletion of exon 4, and have a new amino acid (glycine) generated at the junction. Because this variant was mostly expressed in tumor tissues or the corresponding adjacent noncancerous tissues and not expressed in normal tissues, and this variant possesses very strong effects for promoting tumor growth and metastases, so the invention provides a new tumor therapeutic target and prognostic marker.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

REFERENCE

1. Clark A J, Ishii S, Richert N, Merlino G T, Pastan I. Epidermal growth factor regulates the expression of its own receptor. Proc Natl Acad Sci USA 1985; 82:8374-8378.
2. Merlino G T, Xu Y H, Ishii S, Clark A J, Semba K, Toyoshima K, Yamamoto T, et al. Amplification and enhanced expression of the epidermal growth factor receptor gene in A431 human carcinoma cells. Science 1984; 224: 417-419.
3. Libermann T A, Nusbaum H R, Razon N, Kris R, Lax I, Soreq H, Whittle N, et al. Amplification and overexpression of the EGF receptor gene in primary human glioblastomas. J Cell Sci Suppl 1985; 3: 161-172.
4. Lu S H, Hsieh L L, Luo F C, Weinstein I B. Amplification of the EGF receptor and c-myc genes in human esophageal cancers. Int J Cancer 1988; 42: 502-505.
5. Ro J, North S M, Gallick G E, Hortobagyi G N, Gutterman J U, Blick M. Amplified and overexpressed epidermal growth factor receptor gene in uncultured primary human breast carcinoma. Cancer Res 1988; 48: 161-164.
6. Yoshida K, Tsuda T, Matsumura T, Tsujino T, Hattori T, Ito H, Tahara E. Amplification of epidermal growth factor receptor (EGFR) gene and oncogenes in human gastric carcinomas. Virchows Arch B Cell Pathol Incl Mol Pathol 1989; 57: 285-290.
7. Ishikawa J, Maeda S, Umezu K, Sugiyama T, Kamidono S. Amplification and overexpression of the epidermal growth factor receptor gene in human renal-cell carcinoma. Int J Cancer 1990; 45: 1018-1021.
8. Tsugawa K, Fushida S, Yonemura Y. Amplification of the c-erbB-2 gene in gastric carcinoma: correlation with survival. Oncology 1993; 50: 418-425.
9. Modjtahedi H D C. The receptor for EGF and its ligands: Expression, prognostic value and target for therapy in cancer. Int J Oncol 1994: 277-296.
10. Coussens L, Yang-Feng T L, Liao Y C, Chen E, Gray A, McGrath J, Seeburg P H, et al. Tyrosine kinase receptor with extensive homology to EGF receptor shares chromosomal location with neu oncogene. Science 1985; 230: 1132-1139.
11. Gilmore T, DeClue J E, Martin G S. Protein phosphorylation at tyrosine is induced by the v-erbB gene product in vivo and in vitro. Cell 1985; 40:609-618.
12. Adelsman M A, Huntley B K, Maihle N J. Ligand-independent dimerization of oncogenic v-erbB products involves covalent interactions. J Virol 1996; 70: 2533-2544.
13. Khazaie K, Dull T J, Graf T, Schlessinger J, Ullrich A, Beug H, Vennstrom B. Truncation of the human EGF receptor leads to differential transforming potentials in primary avian fibroblasts and erythroblasts. Embo J 1988; 7: 3061-3071.
14. Collins V P. Amplified genes in human gliomas. Semin Cancer Biol 1993; 4: 27-32.
15. Kleihues P, Lubbe J, Watanabe K, von Ammon K, Ohgaki H. Genetic alterations associated with glioma progression. Verh Dtsch Ges Pathol 1994; 78: 43-47.
16. Viana-Pereira M, Lopes J M, Little S, Milanezi F, Basto D, Pardal F, Jones C, et al. Analysis of EGFR overexpression, EGFR gene amplification and the EGFRvIII mutation in Portuguese high-grade gliomas, Anticancer Res 2008; 28: 913-920.
17. Goike H M, Asplund A C, Pettersson E H, Liu L, Sanoudou D, Collins V P. Acquired rearrangement of an amplified epidermal growth factor receptor (EGFR) gene in a human glioblastoma xenograft. J Neuropathol Exp Neurol 1999; 58:697-701.
18. Schwechheimer K, Huang S, Cavenee W K. EGFR gene amplification-rearrangement in human glioblastomas. Int J Cancer 1995; 62: 145-148.

19. Zhang X, Silva E, Gershenson D, Hung M C. Amplification and rearrangement of c-erb B proto-oncogenes in cancer of human female genital tract. Oncogene 1989; 4:985-989.
20. Libermann T A, Nusbaum H R, Razon N, Kris R, Lax I, Soreq H, Whittle N, et al. Amplification, enhanced expression and possible rearrangement of EGF receptor gene in primary human brain tumours of glial origin. Nature 1985; 313: 144-147.
21. Kuan C T, Wikstrand C J, Bigner D D. EGF mutant receptor vIII as a molecular target in cancer therapy. Endocr Relat Cancer 2001; 8:83-96.
22. Pedersen M W, Meltorn M, Damstrup L, Poulsen H S. The type III epidermal growth factor receptor mutation. Biological significance and potential target for anti-cancer therapy. Ann Oncol 2001; 12: 745-760.
23. Zhou M, Gong B, Gu J, Li Z. EGFRvIII mRNA detection in the serum of patients with hepatocellular carcinoma. Liver Int 2010; 30:925-927.
24. Wang H, Jiang H, Zhou M, Xu Z, Liu S, Shi B, Yao X, et al. Epidermal growth factor receptor vIII enhances tumorigenicity and resistance to 5-fluorouracil in human hepatocellular carcinoma. Cancer Lett 2009; 279: 30-38.

What is claimed:

1. An isolated polypeptide of human epidermal growth factor receptor variant de4 EGFR selected from the group consisting of:
   (a) a polypeptide comprising the amino acid sequence of SEQ ID NO: 2;
   (b) a polypeptide generated by a replacement of 1-10 amino acids, a deletion of 1-10 amino acids or an addition of less than 10 amino acids at the C-terminal end and/or the N-terminal end of SEQ ID NO: 2, which can promote tumor cell invasion and/or migration and is derived from (a); and
   (c) a polypeptide possessing ≥98% homology to the amino acid sequence of SEQ ID NO: 2, which can promote tumor cell invasion or migration and is derived from (a).

2. The polypeptide according to claim 1, wherein the amino acid sequence of the polypeptide is SEQ ID NO: 2.

3. The polypeptide according to claim 1, wherein said replacement is a replacement of 1-10 amino acids with the amino acids having substantially the same or similar property, as compared with those of SEQ ID NO: 2.

4. The polypeptide according to claim 3, wherein said replacement is a replacement of 1-8 amino acids.

5. The polypeptide according to claim 4, wherein said replacement is a replacement of 1-5 amino acids.

6. The polypeptide according to claim 5, wherein said replacement is a replacement of 1-3 amino acids.

7. The polypeptide according to claim 3, wherein said replacement is a replacement of 1-10 amino acids according to the following:

| Original residue in SEQ ID NO: 2 | replacement residue |
|---|---|
| Ala (A) | Val; Leu; or Ile |
| Arg I | Lys; Gln; or Asn |
| Asn (N) | Gln; His; Lys; or Arg |
| Asp (D) | Glu |
| Cys (C) | Ser |
| Gln (Q) | Asn |
| Glu I | Asp |
| Gly (G) | Pro; or Ala |
| His (H) | Asn; Gln; Lys; or Arg |
| Ile (I) | Leu; Val; Met; Ala; or Phe |
| Leu (L) | Ile; Val; Met; Ala; or Phe |
| Lys (K) | Arg; Gln; or Asn |
| Met (M) | Leu; Phe; or Ile |
| Phe (F) | Leu; Val; Ile; Ala; or Tyr |
| Pro (P) | Ala. |

8. The polypeptide according to claim 3, wherein said replacement is a replacement of 1-10 amino according to the following:

| original residue in SEQ ID NO: 2 | replacement residue |
|---|---|
| Ala (A) | Val |
| Arg (R) | Lys |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile |
| Lys (K) | Arg |
| Met (M) | Leu |
| Phe (F) | Leu |
| Pro (P) | Ala. |

* * * * *

SEQUENCE LISTING

<160> NUMBER OF SEQ ID NOS: 21

<210> SEQ ID NO 1
<211> LENGTH: 3498
<212> TYPE: DNA
<213> ORGANISM: Homo sapiens
<220> FEATURE:
<221> NAME/KEY: CDS
<222> LOCATION: (1)..(3495)

<400> SEQUENCE: 1

```
atg cga ccc tcc ggg acg gcc ggg gca gcg ctc ctg gcg ctg ctg gct      48
Met Arg Pro Ser Gly Thr Ala Gly Ala Ala Leu Leu Ala Leu Leu Ala
1               5                   10                  15 gcg ctc tgc ccg gcg agt cgg gct ctg gag gaa aag aaa gtt tgc caa      96
Ala Leu Cys Pro Ala Ser Arg Ala Leu Glu Glu Lys Lys Val Cys Gln
                20                  25                  30 ggc acg agt aac aag ctc acg cag ttg ggc act ttt gaa gat cat ttt     144
Gly Thr Ser Asn Lys Leu Thr Gln Leu Gly Thr Phe Glu Asp His Phe
            35                  40                  45 ctc agc ctc cag agg atg ttc aat aac tgt gag gtg gtc ctt ggg aat     192
Leu Ser Leu Gln Arg Met Phe Asn Asn Cys Glu Val Val Leu Gly Asn
        50                  55                  60 ttg gaa att acc tat gtg cag agg aat tat gat ctt tcc ttc tta aag     240
Leu Glu Ile Thr Tyr Val Gln Arg Asn Tyr Asp Leu Ser Phe Leu Lys
65                  70                  75                  80 acc atc cag gag gtg gct ggt tat gtc ctc att gcc ctc aac aca gtg     288
Thr Ile Gln Glu Val Ala Gly Tyr Val Leu Ile Ala Leu Asn Thr Val
                85                  90                  95 gag cga att cct ttg gaa aac ctg cag atc atc aga gga aat atg tac     336
Glu Arg Ile Pro Leu Glu Asn Leu Gln Ile Ile Arg Gly Asn Met Tyr
                100                 105                 110 tac gaa aat tcc tat gcc tta gca gtc tta tct aac tat gat gca aat     384
Tyr Glu Asn Ser Tyr Ala Leu Ala Val Leu Ser Asn Tyr Asp Ala Asn
            115                 120                 125 aaa acc gga ctg aag gag ctg ccc atg aga aat tta cag ggc caa aag     432
Lys Thr Gly Leu Lys Glu Leu Pro Met Arg Asn Leu Gln Gly Gln Lys
        130                 135                 140 tgt gat cca agc tgt ccc aat ggg agc tgc tgg ggt gca gga gag gag     480
Cys Asp Pro Ser Cys Pro Asn Gly Ser Cys Trp Gly Ala Gly Glu Glu
145                 150                 155                 160 aac tgc cag aaa ctg acc aaa atc atc tgt gcc cag cag tgc tcc ggg     528
Asn Cys Gln Lys Leu Thr Lys Ile Ile Cys Ala Gln Gln Cys Ser Gly
                165                 170                 175 cgc tgc cgt ggc aag tcc ccc agt gac tgc tgc cac aac cag tgt gct     576
Arg Cys Arg Gly Lys Ser Pro Ser Asp Cys Cys His Asn Gln Cys Ala
                180                 185                 190 gca ggc tgc aca ggc ccc cgg gag agc gac tgc ctg gtc tgc cgc aaa     624
Ala Gly Cys Thr Gly Pro Arg Glu Ser Asp Cys Leu Val Cys Arg Lys
```

```
                195                 200                 205
ttc cga gac gaa gcc acg tgc aag gac acc tgc ccc cca ctc atg ctc    672
Phe Arg Asp Glu Ala Thr Cys Lys Asp Thr Cys Pro Pro Leu Met Leu
    210                 215                 220 tac aac ccc acc acg tac cag atg gat gtg aac ccc gag ggc aaa tac    720
Tyr Asn Pro Thr Thr Tyr Gln Met Asp Val Asn Pro Glu Gly Lys Tyr
225                 230                 235                 240 agc ttt ggt gcc acc tgc gtg aag aag tgt ccc cgt aat tat gtg gtg    768
Ser Phe Gly Ala Thr Cys Val Lys Lys Cys Pro Arg Asn Tyr Val Val
                245                 250                 255 aca gat cac ggc tcg tgc gtc cga gcc tgt ggg gcc gac agc tat gag    816
Thr Asp His Gly Ser Cys Val Arg Ala Cys Gly Ala Asp Ser Tyr Glu
            260                 265                 270 atg gag gaa gac ggc gtc cgc aag tgt aag aag tgc gaa ggg cct tgc    864
Met Glu Glu Asp Gly Val Arg Lys Cys Lys Lys Cys Glu Gly Pro Cys
        275                 280                 285 cgc aaa gtg tgt aac gga ata ggt att ggt gaa ttt aaa gac tca ctc    912
Arg Lys Val Cys Asn Gly Ile Gly Ile Gly Glu Phe Lys Asp Ser Leu
    290                 295                 300 tcc ata aat gct acg aat att aaa cac ttc aaa aac tgc acc tcc atc    960
Ser Ile Asn Ala Thr Asn Ile Lys His Phe Lys Asn Cys Thr Ser Ile
305                 310                 315                 320 agt ggc gat ctc cac atc ctg ccg gtg gca ttt agg ggt gac tcc ttc   1008
Ser Gly Asp Leu His Ile Leu Pro Val Ala Phe Arg Gly Asp Ser Phe
                325                 330                 335 aca cat act cct cct ctg gat cca cag gaa ctg gat att ctg aaa acc   1056
Thr His Thr Pro Pro Leu Asp Pro Gln Glu Leu Asp Ile Leu Lys Thr
            340                 345                 350 gta aag gaa atc aca ggg ttt ttg ctg att cag gct tgg cct gaa aac   1104
Val Lys Glu Ile Thr Gly Phe Leu Leu Ile Gln Ala Trp Pro Glu Asn
        355                 360                 365 agg acg gac ctc cat gcc ttt gag aac cta gaa atc ata cgc ggc agg   1152
Arg Thr Asp Leu His Ala Phe Glu Asn Leu Glu Ile Ile Arg Gly Arg
    370                 375                 380 acc aag caa cat ggt cag ttt tct ctt gca gtc gtc agc ctg aac ata   1200
Thr Lys Gln His Gly Gln Phe Ser Leu Ala Val Val Ser Leu Asn Ile
385                 390                 395                 400 aca tcc ttg gga tta cgc tcc ctc aag gag ata agt gat gga gat gtg   1248
Thr Ser Leu Gly Leu Arg Ser Leu Lys Glu Ile Ser Asp Gly Asp Val
                405                 410                 415 ata att tca gga aac aaa aat ttg tgc tat gca aat aca ata aac tgg   1296
Ile Ile Ser Gly Asn Lys Asn Leu Cys Tyr Ala Asn Thr Ile Asn Trp
            420                 425                 430 aaa aaa ctg ttt ggg acc tcc ggt cag aaa acc aaa att ata agc aac   1344
Lys Lys Leu Phe Gly Thr Ser Gly Gln Lys Thr Lys Ile Ile Ser Asn
        435                 440                 445 aga ggt gaa aac agc tgc aag gcc aca ggc cag gtc tgc cat gcc ttg   1392
Arg Gly Glu Asn Ser Cys Lys Ala Thr Gly Gln Val Cys His Ala Leu
    450                 455                 460 tgc tcc ccc gag ggc tgc tgg ggc ccg gag ccc agg gac tgc gtc tct   1440
Cys Ser Pro Glu Gly Cys Trp Gly Pro Glu Pro Arg Asp Cys Val Ser
465                 470                 475                 480 tgc cgg aat gtc agc cga ggc agg gaa tgc gtg gac aag tgc aac ctt   1488
Cys Arg Asn Val Ser Arg Gly Arg Glu Cys Val Asp Lys Cys Asn Leu
                485                 490                 495 ctg gag ggt gag cca agg gag ttt gtg gag aac tct gag tgc ata cag   1536
Leu Glu Gly Glu Pro Arg Glu Phe Val Glu Asn Ser Glu Cys Ile Gln
            500                 505                 510 tgc cac cca gag tgc ctg cct cag gcc atg aac atc acc tgc aca gga   1584
```

```
                    Cys His Pro Glu Cys Leu Pro Gln Ala Met Asn Ile Thr Cys Thr Gly
                            515                 520                 525 cgg gga cca gac aac tgt atc cag tgt gcc cac tac att gac ggc ccc      1632
Arg Gly Pro Asp Asn Cys Ile Gln Cys Ala His Tyr Ile Asp Gly Pro
        530                 535                 540 cac tgc gtc aag acc tgc ccg gca gga gtc atg gga gaa aac aac acc      1680
His Cys Val Lys Thr Cys Pro Ala Gly Val Met Gly Glu Asn Asn Thr
545                 550                 555                 560 ctg gtc tgg aag tac gca gac gcc ggc cat gtg tgc cac ctg tgc cat      1728
Leu Val Trp Lys Tyr Ala Asp Ala Gly His Val Cys His Leu Cys His
                565                 570                 575 cca aac tgc acc tac gga tgc act ggg cca ggt ctt gaa ggc tgt cca      1776
Pro Asn Cys Thr Tyr Gly Cys Thr Gly Pro Gly Leu Glu Gly Cys Pro
            580                 585                 590 acg aat ggg cct aag atc ccg tcc atc gcc act ggg atg gtg ggg gcc      1824
Thr Asn Gly Pro Lys Ile Pro Ser Ile Ala Thr Gly Met Val Gly Ala
        595                 600                 605 ctc ctc ttg ctg ctg gtg gtg gcc ctg ggg atc ggc ctc ttc atg cga      1872
Leu Leu Leu Leu Leu Val Val Ala Leu Gly Ile Gly Leu Phe Met Arg
610                 615                 620 agg cgc cac atc gtt cgg aag cgc acg ctg cgg agg ctg ctg cag gag      1920
Arg Arg His Ile Val Arg Lys Arg Thr Leu Arg Arg Leu Leu Gln Glu
625                 630                 635                 640 agg gag ctt gtg gag cct ctt aca ccc agt gga gaa gct ccc aac caa      1968
Arg Glu Leu Val Glu Pro Leu Thr Pro Ser Gly Glu Ala Pro Asn Gln
                645                 650                 655 gct ctc ttg agg atc ttg aag gaa act gaa ttc aaa aag atc aaa gtg      2016
Ala Leu Leu Arg Ile Leu Lys Glu Thr Glu Phe Lys Lys Ile Lys Val
            660                 665                 670 ctg ggc tcc ggt gcg ttc ggc acg gtg tat aag gga ctc tgg atc cca      2064
Leu Gly Ser Gly Ala Phe Gly Thr Val Tyr Lys Gly Leu Trp Ile Pro
        675                 680                 685 gaa ggt gag aaa gtt aaa att ccc gtc gct atc aag gaa tta aga gaa      2112
Glu Gly Glu Lys Val Lys Ile Pro Val Ala Ile Lys Glu Leu Arg Glu
690                 695                 700 gca aca tct ccg aaa gcc aac aag gaa atc ctc gat gaa gcc tac gtg      2160
Ala Thr Ser Pro Lys Ala Asn Lys Glu Ile Leu Asp Glu Ala Tyr Val
705                 710                 715                 720 atg gcc agc gtg gac aac ccc cac gtg tgc cgc ctg ctg ggc atc tgc      2208
Met Ala Ser Val Asp Asn Pro His Val Cys Arg Leu Leu Gly Ile Cys
                725                 730                 735 ctc acc tcc acc gtg cag ctc atc acg cag ctc atg ccc ttc ggc tgc      2256
Leu Thr Ser Thr Val Gln Leu Ile Thr Gln Leu Met Pro Phe Gly Cys
            740                 745                 750 ctc ctg gac tat gtc cgg gaa cac aaa gac aat att ggc tcc cag tac      2304
Leu Leu Asp Tyr Val Arg Glu His Lys Asp Asn Ile Gly Ser Gln Tyr
        755                 760                 765 ctg ctc aac tgg tgt gtg cag atc gca aag ggc atg aac tac ttg gag      2352
Leu Leu Asn Trp Cys Val Gln Ile Ala Lys Gly Met Asn Tyr Leu Glu
770                 775                 780 gac cgt cgc ttg gtg cac cgc gac ctg gca gcc agg aac gta ctg gtg      2400
Asp Arg Arg Leu Val His Arg Asp Leu Ala Ala Arg Asn Val Leu Val
785                 790                 795                 800 aaa aca ccg cag cat gtc aag atc aca gat ttt ggg ctg gcc aaa ctg      2448
Lys Thr Pro Gln His Val Lys Ile Thr Asp Phe Gly Leu Ala Lys Leu
                805                 810                 815 ctg ggt gcg gaa gag aaa gaa tac cat gca gaa gga ggc aaa gtg cct      2496
Leu Gly Ala Glu Glu Lys Glu Tyr His Ala Glu Gly Gly Lys Val Pro
            820                 825                 830
```

```
atc aag tgg atg gca ttg gaa tca att tta cac aga atc tat acc cac    2544
Ile Lys Trp Met Ala Leu Glu Ser Ile Leu His Arg Ile Tyr Thr His
        835                 840                 845 cag agt gat gtc tgg agc tac ggg gtg acc gtt tgg gag ttg atg acc    2592
Gln Ser Asp Val Trp Ser Tyr Gly Val Thr Val Trp Glu Leu Met Thr
850                 855                 860 ttt gga tcc aag cca tat gac gga atc cct gcc agc gag atc tcc tcc    2640
Phe Gly Ser Lys Pro Tyr Asp Gly Ile Pro Ala Ser Glu Ile Ser Ser
865                 870                 875                 880 atc ctg gag aaa gga gaa cgc ctc cct cag cca ccc ata tgt acc atc    2688
Ile Leu Glu Lys Gly Glu Arg Leu Pro Gln Pro Pro Ile Cys Thr Ile
                885                 890                 895 gat gtc tac atg atc atg gtc aag tgc tgg atg ata gac gca gat agt    2736
Asp Val Tyr Met Ile Met Val Lys Cys Trp Met Ile Asp Ala Asp Ser
            900                 905                 910 cgc cca aag ttc cgt gag ttg atc atc gaa ttc tcc aaa atg gcc cga    2784
Arg Pro Lys Phe Arg Glu Leu Ile Ile Glu Phe Ser Lys Met Ala Arg
        915                 920                 925 gac ccc cag cgc tac ctt gtc att cag ggg gat gaa aga atg cat ttg    2832
Asp Pro Gln Arg Tyr Leu Val Ile Gln Gly Asp Glu Arg Met His Leu
930                 935                 940 cca agt cct aca gac tcc aac ttc tac cgt gcc ctg atg gat gaa gaa    2880
Pro Ser Pro Thr Asp Ser Asn Phe Tyr Arg Ala Leu Met Asp Glu Glu
945                 950                 955                 960 gac atg gac gac gtg gtg gat gcc gac gag tac ctc atc cca cag cag    2928
Asp Met Asp Asp Val Val Asp Ala Asp Glu Tyr Leu Ile Pro Gln Gln
                965                 970                 975 ggc ttc ttc agc agc ccc tcc acg tca cgg act ccc ctc ctg agc tct    2976
Gly Phe Phe Ser Ser Pro Ser Thr Ser Arg Thr Pro Leu Leu Ser Ser
            980                 985                 990 ctg agt gca acc agc aac aat tcc acc gtg gct tgc att gat aga aat    3024
Leu Ser Ala Thr Ser Asn Asn Ser Thr Val Ala Cys Ile Asp Arg Asn
        995                 1000                1005 ggg ctg caa agc tgt ccc atc aag gaa gac agc ttc ttg cag cga        3069
Gly Leu Gln Ser Cys Pro Ile Lys Glu Asp Ser Phe Leu Gln Arg
    1010                1015                1020 tac agc tca gac ccc aca ggc gcc ttg act gag gac agc ata gac        3114
Tyr Ser Ser Asp Pro Thr Gly Ala Leu Thr Glu Asp Ser Ile Asp
    1025                1030                1035 gac acc ttc ctc cca gtg cct gaa tac ata aac cag tcc gtt ccc        3159
Asp Thr Phe Leu Pro Val Pro Glu Tyr Ile Asn Gln Ser Val Pro
    1040                1045                1050 aaa agg ccc gct ggc tct gtg cag aat cct gtc tat cac aat cag        3204
Lys Arg Pro Ala Gly Ser Val Gln Asn Pro Val Tyr His Asn Gln
    1055                1060                1065 cct ctg aac ccc gcg ccc agc aga gac cca cac tac cag gac ccc        3249
Pro Leu Asn Pro Ala Pro Ser Arg Asp Pro His Tyr Gln Asp Pro
    1070                1075                1080 cac agc act gca gtg ggc aac ccc gag tat ctc aac act gtc cag        3294
His Ser Thr Ala Val Gly Asn Pro Glu Tyr Leu Asn Thr Val Gln
    1085                1090                1095 ccc acc tgt gtc aac agc aca ttc gac agc cct gcc cac tgg gcc        3339
Pro Thr Cys Val Asn Ser Thr Phe Asp Ser Pro Ala His Trp Ala
    1100                1105                1110 cag aaa ggc agc cac caa att agc ctg gac aac cct gac tac cag        3384
Gln Lys Gly Ser His Gln Ile Ser Leu Asp Asn Pro Asp Tyr Gln
    1115                1120                1125 cag gac ttc ttt ccc aag gaa gcc aag cca aat ggc atc ttt aag        3429
Gln Asp Phe Phe Pro Lys Glu Ala Lys Pro Asn Gly Ile Phe Lys
    1130                1135                1140
```

-continued

```
ggc tcc aca gct gaa aat gca gaa tac cta agg gtc gcg cca caa    3474
Gly Ser Thr Ala Glu Asn Ala Glu Tyr Leu Arg Val Ala Pro Gln
    1145                1150                1155 agc agt gaa ttt att gga gca tga                                3498
Ser Ser Glu Phe Ile Gly Ala
    1160            1165
```

<210> SEQ ID NO 2
<211> LENGTH: 1165
<212> TYPE: PRT
<213> ORGANISM: Homo sapiens

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Gly Gln Lys
    130                 135                 140

Cys Asp Pro Ser Cys Pro Asn Gly Ser Cys Trp Gly Ala Gly Glu Glu
145                 150                 155                 160

Asn Cys Gln Lys Leu Thr Lys Ile Ile Cys Ala Gln Gln Cys Ser Gly
                165                 170                 175

Arg Cys Arg Gly Lys Ser Pro Ser Asp Cys Cys His Asn Gln Cys Ala
            180                 185                 190

Ala Gly Cys Thr Gly Pro Arg Glu Ser Asp Cys Leu Val Cys Arg Lys
        195                 200                 205

Phe Arg Asp Glu Ala Thr Cys Lys Asp Thr Cys Pro Pro Leu Met Leu
    210                 215                 220

Tyr Asn Pro Thr Thr Tyr Gln Met Asp Val Asn Pro Glu Gly Lys Tyr
225                 230                 235                 240

Ser Phe Gly Ala Thr Cys Val Lys Lys Cys Pro Arg Asn Tyr Val Val
                245                 250                 255

Thr Asp His Gly Ser Cys Val Arg Ala Cys Gly Ala Asp Ser Tyr Glu
            260                 265                 270

Met Glu Glu Asp Gly Val Arg Lys Cys Lys Lys Cys Glu Gly Pro Cys
        275                 280                 285

Arg Lys Val Cys Asn Gly Ile Gly Ile Gly Glu Phe Lys Asp Ser Leu
    290                 295                 300

Ser Ile Asn Ala Thr Asn Ile Lys His Phe Lys Asn Cys Thr Ser Ile
305                 310                 315                 320

Ser Gly Asp Leu His Ile Leu Pro Val Ala Phe Arg Gly Asp Ser Phe
                325                 330                 335

```
Thr His Thr Pro Pro Leu Asp Pro Gln Glu Leu Asp Ile Leu Lys Thr
            340                 345                 350

Val Lys Glu Ile Thr Gly Phe Leu Ile Gln Ala Trp Pro Glu Asn
            355                 360                 365

Arg Thr Asp Leu His Ala Phe Glu Asn Leu Glu Ile Ile Arg Gly Arg
    370                 375                 380

Thr Lys Gln His Gly Gln Phe Ser Leu Ala Val Val Ser Leu Asn Ile
385                 390                 395                 400

Thr Ser Leu Gly Leu Arg Ser Leu Lys Glu Ile Ser Asp Gly Asp Val
                405                 410                 415

Ile Ile Ser Gly Asn Lys Asn Leu Cys Tyr Ala Asn Thr Ile Asn Trp
            420                 425                 430

Lys Lys Leu Phe Gly Thr Ser Gly Gln Lys Thr Lys Ile Ile Ser Asn
            435                 440                 445

Arg Gly Glu Asn Ser Cys Lys Ala Thr Gly Gln Val Cys His Ala Leu
    450                 455                 460

Cys Ser Pro Glu Gly Cys Trp Gly Pro Glu Pro Arg Asp Cys Val Ser
465                 470                 475                 480

Cys Arg Asn Val Ser Arg Gly Arg Glu Cys Val Asp Lys Cys Asn Leu
                485                 490                 495

Leu Glu Gly Glu Pro Arg Glu Phe Val Glu Asn Ser Glu Cys Ile Gln
            500                 505                 510

Cys His Pro Glu Cys Leu Pro Gln Ala Met Asn Ile Thr Cys Thr Gly
            515                 520                 525

Arg Gly Pro Asp Asn Cys Ile Gln Cys Ala His Tyr Ile Asp Gly Pro
    530                 535                 540

His Cys Val Lys Thr Cys Pro Ala Gly Val Met Gly Glu Asn Asn Thr
545                 550                 555                 560

Leu Val Trp Lys Tyr Ala Asp Ala Gly His Val Cys His Leu Cys His
                565                 570                 575

Pro Asn Cys Thr Tyr Gly Cys Thr Gly Pro Gly Leu Glu Gly Cys Pro
            580                 585                 590

Thr Asn Gly Pro Lys Ile Pro Ser Ile Ala Thr Gly Met Val Gly Ala
            595                 600                 605

Leu Leu Leu Leu Leu Val Val Ala Leu Gly Ile Gly Leu Phe Met Arg
    610                 615                 620

Arg Arg His Ile Val Arg Lys Arg Thr Leu Arg Arg Leu Leu Gln Glu
625                 630                 635                 640

Arg Glu Leu Val Glu Pro Leu Thr Pro Ser Gly Glu Ala Pro Asn Gln
                645                 650                 655

Ala Leu Leu Arg Ile Leu Lys Glu Thr Glu Phe Lys Lys Ile Lys Val
            660                 665                 670

Leu Gly Ser Gly Ala Phe Gly Thr Val Tyr Lys Gly Leu Trp Ile Pro
            675                 680                 685

Glu Gly Glu Lys Val Lys Ile Pro Val Ala Ile Lys Glu Leu Arg Glu
    690                 695                 700

Ala Thr Ser Pro Lys Ala Asn Lys Glu Ile Leu Asp Glu Ala Tyr Val
705                 710                 715                 720

Met Ala Ser Val Asp Asn Pro His Val Cys Arg Leu Leu Gly Ile Cys
                725                 730                 735

Leu Thr Ser Thr Val Gln Leu Ile Thr Gln Leu Met Pro Phe Gly Cys
            740                 745                 750
```

```
Leu Leu Asp Tyr Val Arg Glu His Lys Asp Asn Ile Gly Ser Gln Tyr
    755                 760                 765

Leu Leu Asn Trp Cys Val Gln Ile Ala Lys Gly Met Asn Tyr Leu Glu
    770                 775                 780

Asp Arg Arg Leu Val His Arg Asp Leu Ala Ala Arg Asn Val Leu Val
785                 790                 795                 800

Lys Thr Pro Gln His Val Lys Ile Thr Asp Phe Gly Leu Ala Lys Leu
                805                 810                 815

Leu Gly Ala Glu Lys Glu Tyr His Ala Gly Gly Lys Val Pro
                820                 825                 830

Ile Lys Trp Met Ala Leu Glu Ser Ile Leu His Arg Ile Tyr Thr His
        835                 840                 845

Gln Ser Asp Val Trp Ser Tyr Gly Val Thr Val Trp Glu Leu Met Thr
    850                 855                 860

Phe Gly Ser Lys Pro Tyr Asp Gly Ile Pro Ala Ser Glu Ile Ser Ser
865                 870                 875                 880

Ile Leu Glu Lys Gly Glu Arg Leu Pro Gln Pro Pro Ile Cys Thr Ile
                885                 890                 895

Asp Val Tyr Met Ile Met Val Lys Cys Trp Met Ile Asp Ala Asp Ser
                900                 905                 910

Arg Pro Lys Phe Arg Glu Leu Ile Ile Glu Phe Ser Lys Met Ala Arg
        915                 920                 925

Asp Pro Gln Arg Tyr Leu Val Ile Gln Gly Asp Glu Arg Met His Leu
    930                 935                 940

Pro Ser Pro Thr Asp Ser Asn Phe Tyr Arg Ala Leu Met Asp Glu Glu
945                 950                 955                 960

Asp Met Asp Asp Val Val Asp Ala Asp Glu Tyr Leu Ile Pro Gln Gln
                965                 970                 975

Gly Phe Phe Ser Ser Pro Ser Thr Ser Arg Thr Pro Leu Leu Ser Ser
                980                 985                 990

Leu Ser Ala Thr Ser Asn Asn Ser Thr Val Ala Cys Ile Asp Arg Asn
        995                 1000                1005

Gly Leu Gln Ser Cys Pro Ile Lys Glu Asp Ser Phe Leu Gln Arg
    1010                1015                1020

Tyr Ser Ser Asp Pro Thr Gly Ala Leu Thr Glu Asp Ser Ile Asp
    1025                1030                1035

Asp Thr Phe Leu Pro Val Pro Glu Tyr Ile Asn Gln Ser Val Pro
    1040                1045                1050

Lys Arg Pro Ala Gly Ser Val Gln Asn Pro Val Tyr His Asn Gln
    1055                1060                1065

Pro Leu Asn Pro Ala Pro Ser Arg Asp Pro His Tyr Gln Asp Pro
    1070                1075                1080

His Ser Thr Ala Val Gly Asn Pro Glu Tyr Leu Asn Thr Val Gln
    1085                1090                1095

Pro Thr Cys Val Asn Ser Thr Phe Asp Ser Pro Ala His Trp Ala
    1100                1105                1110

Gln Lys Gly Ser His Gln Ile Ser Leu Asp Asn Pro Asp Tyr Gln
    1115                1120                1125

Gln Asp Phe Phe Pro Lys Glu Ala Lys Pro Asn Gly Ile Phe Lys
    1130                1135                1140

Gly Ser Thr Ala Glu Asn Ala Glu Tyr Leu Arg Val Ala Pro Gln
    1145                1150                1155

Ser Ser Glu Phe Ile Gly Ala
```

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
gtattgatcg ggagagccg                                                    19

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
gtggagatcg ccactgatg                                                    19

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cccatgagaa atttacaggg c                                                 21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
gtggtggggt tgtagagcat g                                                 21

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
gtattgatcg ggagagccg                                                    19

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
tgacttgata cagtaccgat ccgg                                              24

<210> SEQ ID NO 9
<211> LENGTH: 21
<212> TYPE: DNA
<213> ORGANISM: Artificial Sequence

```
<220> FEATURE:
<223> OTHER INFORMATION: primer

<400> SEQUENCE: 9
cccatgagaa atttacaggg c                                           21

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
tgacttgata cagtaccgat ccgg                                        24

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
caacagaggt acagcaaaca accag                                       25

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
gtattgatcg ggagagccg                                              19

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
gtggagatcg ccactgatg                                              19

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
catccagtgg cgggacatag                                             20

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
gtggtggggt tgtagagcat g                                           21
```

```
<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
gtattgatcg ggagagccg                                                   19

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
tgacttgata cagtaccgat ccgg                                             24

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
atgcgaccct ccgggacg                                                    18

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
ggaatcaagc atcctctgga agac                                             24

<210> SEQ ID NO 20
<211> LENGTH: 22
<212> TYPE: PRT
<213> ORGANISM: Homo sapiens

<400> SEQUENCE: 20

Cys Ser Thr Ala Glu Asn Ala Glu Tyr Leu Arg Val Ala Pro Gln Ser
1               5                   10                  15

Ser Glu Phe Ile Gly Ala
            20

<210> SEQ ID NO 21
<211> LENGTH: 7
<212> TYPE: PRT
<213> ORGANISM: Homo sapiens

<400> SEQUENCE: 21

Asn Leu Gln Gly Gln Lys Cys
1               5
```